(12) United States Patent
Kroupa

(10) Patent No.: US 8,656,913 B2
(45) Date of Patent: Feb. 25, 2014

(54) VENTILATOR APPARATUS

(75) Inventor: Kevin D. Kroupa, Ballwin, MO (US)

(73) Assignee: Allied Healthcare Products, Inc., St. Louis, MO (US)

( * ) Notice: Subject to any disclaimer, the term of this patent is extended or adjusted under 35 U.S.C. 154(b) by 1077 days.

(21) Appl. No.: 11/810,214

(22) Filed: Jun. 5, 2007

(65) Prior Publication Data

US 2008/0302363 A1 Dec. 11, 2008

(51) Int. Cl.
*A61M 16/00* (2006.01)
*A62B 7/00* (2006.01)
*F16K 31/02* (2006.01)

(52) U.S. Cl.
USPC ............. 128/204.18; 128/204.21; 128/204.23

(58) Field of Classification Search
USPC ............. 128/204.18, 204.21, 204.22, 205.24, 128/204.23
See application file for complete search history.

(56) References Cited

U.S. PATENT DOCUMENTS

| | | | |
|---|---|---|---|
| 4,001,700 A | | 1/1977 | Cook et al. |
| 4,057,059 A | | 11/1977 | Reid et al. |
| 4,182,599 A | * | 1/1980 | Eyrick et al. ................. 417/328 |
| 4,256,100 A | | 3/1981 | Levy et al. |
| 4,323,064 A | * | 4/1982 | Hoenig et al. ........... 128/204.21 |
| 4,380,233 A | | 4/1983 | Caillot |
| 4,381,774 A | * | 5/1983 | Schreiber et al. ........ 128/202.22 |
| 4,401,116 A | * | 8/1983 | Fry et al. .................. 128/205.24 |
| 4,867,152 A | | 9/1989 | Kou et al. |
| 4,898,174 A | | 2/1990 | Fangrow |
| 4,905,688 A | | 3/1990 | Vicenzi et al. |
| 5,211,170 A | * | 5/1993 | Press ......................... 128/204.18 |
| 5,303,699 A | | 4/1994 | Bonassa et al. |
| 5,458,124 A | * | 10/1995 | Stanko et al. ................. 600/509 |
| 5,494,028 A | | 2/1996 | DeVries et al. |
| 5,540,220 A | | 7/1996 | Gropper et al. |
| 5,839,434 A | * | 11/1998 | Enterline .................. 128/204.23 |
| 6,055,981 A | * | 5/2000 | Laswick et al. ........... 128/204.18 |
| 6,390,091 B1 | | 5/2002 | Banner et al. |
| 6,526,970 B2 | | 3/2003 | DeVries et al. |

(Continued)

FOREIGN PATENT DOCUMENTS

| | | |
|---|---|---|
| JP | H-07-299144 A | 11/1995 |
| WO | WO2006/026335 | 3/2006 |
| WO | WO2008/153867 | 12/2008 |

OTHER PUBLICATIONS

Freescale Semiconductor, Inc., Integrated Silicon Pressure Sensor On-Chip Conditioned, Temperature Compensated and Calibrated, MPXV4006G, May 2005, Rev. 5.

(Continued)

*Primary Examiner* — Kristen Matter
(74) *Attorney, Agent, or Firm* — Christopher R. Carroll; The Small Patent Law Group LLC

(57) ABSTRACT

One or more embodiments of the presently described invention provides a ventilator including a timing device, an electric power source and a flow control device. The timing device is electronically controlled and is capable of controlling a period of time that a fluid is delivered to a patient. The timing device can control this period of time using a solenoid. The flow control device controls a rate of flow that the fluid is delivered to the patient. The flow control device can control the rate of flow using a plurality of orifices. The timing device and flow control device are separate from one another and each is capable of being operated independent of the other.

22 Claims, 14 Drawing Sheets

(56) References Cited

U.S. PATENT DOCUMENTS

| | | |
|---|---|---|
| 6,622,753 B2 * | 9/2003 | Thordarson et al. .......... 137/613 |
| 7,530,353 B2 * | 5/2009 | Choncholas et al. .... 128/204.18 |
| 2002/0185127 A1 * | 12/2002 | Melker et al. ............ 128/202.22 |
| 2004/0200477 A1 | 10/2004 | Bleys et al. |
| 2005/0066968 A1 | 3/2005 | Shofner et al. |
| 2005/0066976 A1 * | 3/2005 | Wondka ................... 128/207.18 |
| 2005/0126578 A1 | 6/2005 | Garrison et al. |
| 2007/0000490 A1 | 1/2007 | DeVries et al. |
| 2007/0062533 A1 * | 3/2007 | Choncholas et al. .... 128/204.23 |
| 2009/0084381 A1 * | 4/2009 | DeVries et al. .......... 128/204.21 |
| 2009/0133697 A1 * | 5/2009 | Kwok et al. ............. 128/205.25 |

OTHER PUBLICATIONS

Presairtrol, LLC, Printed Circuit Boards, Part No. CSPSEGA-10PR(60 4).

ISR and W/O for PCT/US2008/07003 dated Oct. 2, 2008.

* cited by examiner

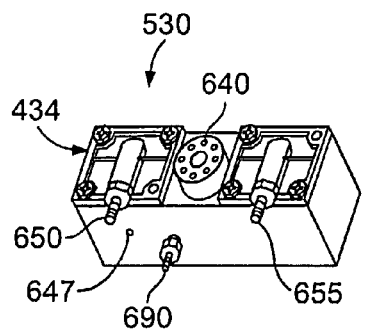
FIG. 5A
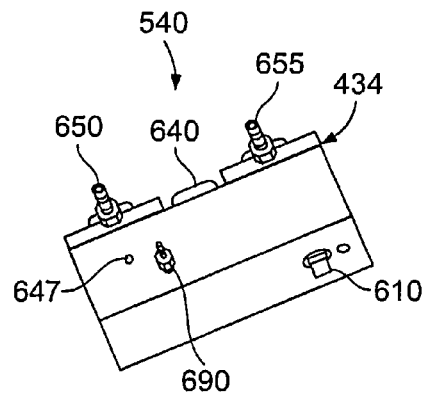
FIG. 5B
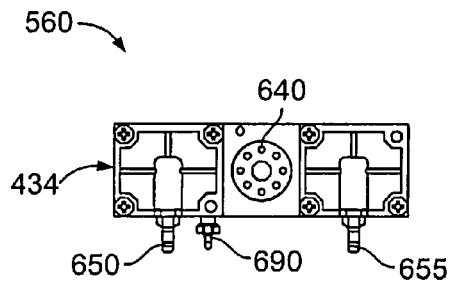
FIG. 5C
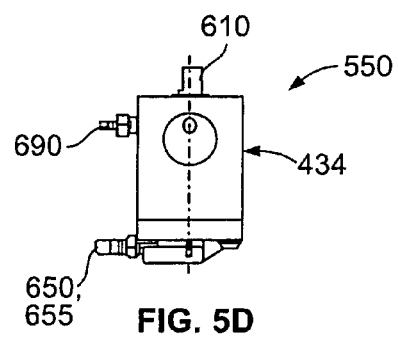
FIG. 5D
FIGURE 5

FIG. 10A
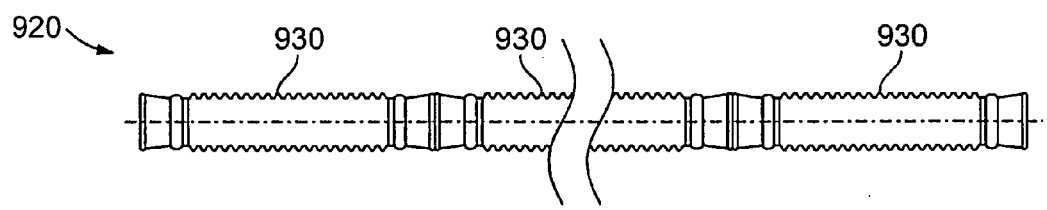
FIG. 10B
FIGURE 10

VENTILATOR APPARATUS

CROSS-REFERENCE TO RELATED APPLICATIONS

Not applicable.

BACKGROUND OF THE INVENTION

The presently described invention generally relates to artificial breathing devices. More specifically, embodiments of the presently described technology provide an improved ventilator apparatus.

Emergency ventilators are devices that can partially or entirely replace bag mask resuscitation devices as a manner of providing mechanical ventilation in an emergency environment. Existing devices can permit the user, such as an EMT or paramedic, to set a tidal volume ("$V_T$") and breaths per minute ("BPM") and little more, if anything. These existing devices are usually driven or powered by oxygen under pressure flowing from portable compressed oxygen cylinders.

Existing hospital ventilators can be difficult to use by individuals who are not as highly trained as respiratory therapists. In addition, existing ventilators can be very expensive. Given new requirements on hospitals to prepare for events such as terrorist attacks, natural disasters or an outbreak of disease such as avian flu, adding large numbers of ventilators can be a large financial burden and having adequate trained staffing during such a crisis can be a bigger problem.

Existing ventilators typically are controlled by a complex electronic system ("electric-only ventilators") or by a complex system of pneumatics ("pneumatic-only ventilators"). With respect to the electric-only ventilators, these devices suffer from many drawbacks. For example, electric-only ventilators usually include a fragile electronic system of circuits used to control inspiration time and fluid flow through the ventilator. As a result, these types of ventilators tend to be relatively fragile when compared to pneumatically controlled ventilators. As emergency ventilators are typically used in emergency situations, the durability of the ventilators is of considerable importance.

Electric-only ventilators also usually include electronic circuits to control and drive a complex proportioning valve to set the fluid flow through the ventilator. Controlling such a valve typically requires a considerable amount of electric power. As a result, electric-only ventilators are usually powered by a lead acid or lithium ion battery. These types of batteries are relatively heavy and are not easily accessible during emergency situations. That is, in an emergency situation, a supply of lead acid or lithium ion batteries may not be readily available. Moreover, existing electric-only ventilators can deplete a lead acid or lithium ion battery fairly quickly. Many ventilators can deplete such a battery in under eight hours.

In addition, use of such a valve typically requires one or more position feedback circuits to achieve the accuracy required of a ventilator. The added complexity of position feedback circuits only adds to the cost of these types of ventilators.

With respect to pneumatic-only ventilators, these devices tend to be more durable than electric-only ventilators (most likely because they do not include the complex circuitry of electric-only ventilators). But, pneumatic-only ventilators usually must be very closely monitored during operation. These ventilators use a system of pneumatics powered by the fluid being delivered to the patient to control timing and flow of the fluid through the ventilator. That is, the ventilators use a build up of pressure in the device as a timing function. With small leaks and/or changes in the source fluid pressure, the timing function and thus the ventilator can suffer from poor precision and/or accuracy. Pneumatic ventilators cost less than complex electronic ventilators but still cost several thousand dollars due to the pneumatic components required.

While some more inexpensive ventilators have been introduced into the market, these ventilators also suffer from drawbacks. For example, one or more of these ventilators do not include any feedback to a user of the ventilator. That is, a user cannot determine the BPM or volume of fluid being delivered to a patient. The user must externally calculate such information using, for example, a stopwatch to determine the total time of inspiration. With such ventilators, a single user cannot assist more than one person in emergency situations. The user must stay with a ventilator to continually monitor its delivery of fluid to a user.

Thus, a need exists for an improved ventilator that is cheaper to manufacture, more durable, more precise and more accurate.

BRIEF SUMMARY OF THE INVENTION

One or more embodiments of the presently described invention provides a ventilator including a timing device, an electric power source and a flow control device. The timing device is capable of controlling a period of time that a fluid is delivered to a patient. The timing device can control this period of time using a solenoid. The flow control device controls a rate of flow that the fluid is delivered to the patient. The flow control device can control the rate of flow using a plurality of orifices.

One or more embodiments of the presently described invention also provides a method for providing improved control of a ventilator. The method includes the steps of electronically controlling a period of time that a fluid is delivered to a patient using a solenoid, controlling a rate of flow that the fluid is delivered to the patient by directing the fluid through at least one of a plurality of orifices having a plurality of different diameters, and providing a volume of the fluid to the patient by permitting the fluid to pass through the ventilator at the rate of flow for the period of time.

One or more embodiments of the presently described invention also provide a ventilator including an inspiratory timing control device and a plurality of orifices. The timing control device is configured to start and stop a flow of fluid through the ventilator and is powered by at least one battery. The orifices include different diameters and are configured to control a rate of fluid flow through the ventilator.

BRIEF DESCRIPTION OF THE SEVERAL VIEWS OF THE DRAWINGS

FIGS. 5A, 5B, 5C, and 5D illustrate several views of a flow control device in accordance with an embodiment of the presently described invention.

FIGS. 10A and 10B illustrate views of tubing capable of being used as a patent circuit connection in accordance with an embodiment of the presently described invention.

Figure 1:
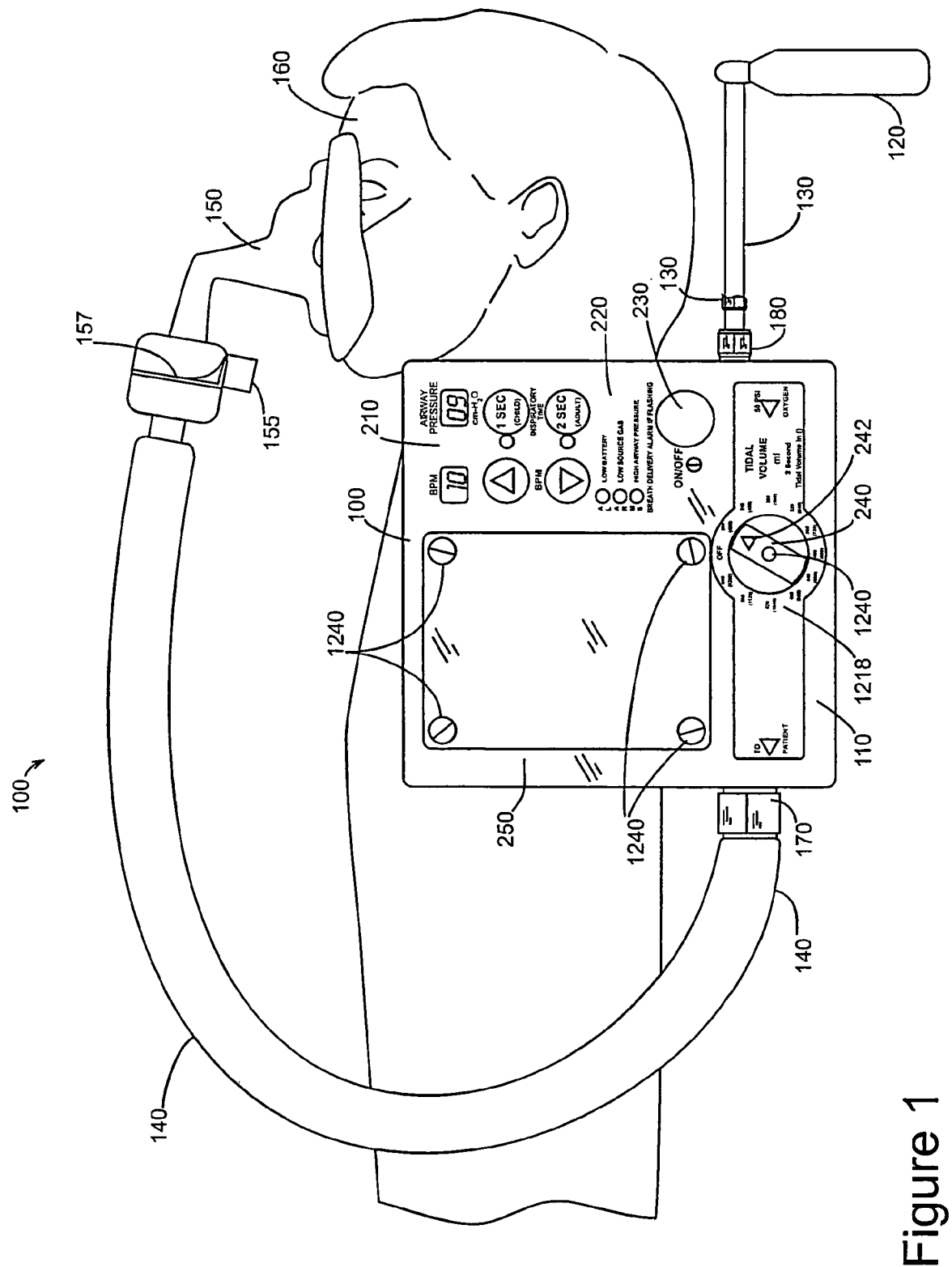
FIG. 1 illustrates a diagram of a ventilator system in accordance with an embodiment of the presently described invention.

The foregoing summary, as well as the following detailed description of certain embodiments of the presently described technology, will be better understood when read in conjunction with the appended drawings. For the purpose of illustrating the presently described technology, certain embodiments are shown in the drawings. It should be understood, however, that the presently described technology is not limited to the arrangements and instrumentality shown in the attached drawings.

DETAILED DESCRIPTION OF THE INVENTION

FIG. 1 illustrates a diagram of a ventilator system 100 in accordance with an embodiment of the presently described invention. Ventilator system 100 includes a ventilator device 110, a fluid source 120, a fluid source connection 130, a patient circuit connection 140, a delivery device 150, an output valve 170 and an input or inlet valve 180. As shown in FIG. 1, ventilator system 100 is connected to a patient 160.

Fluid source 120 is connected to ventilator 110 by way of fluid source connection 130. Ventilator 110 is connected with delivery device 150 by way of patient circuit connection 140. Delivery device 150 is connected to patient 160. In an embodiment, delivery device 150 includes an exhalation port 155 and/or a one-way valve 157. One-way valve 157 can include a valve that only permits the flow of fluid in one direction through valve 157 and, once the pressure of the fluid flowing through valve 157 drops a sufficient amount, valve 157 closes. For example, one-way valve 157 can comprise a duck valve or duck bill valve.

Fluid source 120 can include any container holding a fluid that is to be delivered to patient 160 using ventilator 110. For example, fluid source 120 can include a canister of pressurized gas. In an embodiment, fluid source 120 includes a pressurized canister of oxygen. In another embodiment, fluid source 120 includes a 280 kPa (40.6 psi) to 600 kPa (87.0 psi) oxygen canister. In another embodiment, fluid source 120 includes a 344 kPa (50.0 psi oxygen canister with a minimum of 40 liters per minute flow capacity. In another embodiment, fluid source 120 includes a high flow air and oxygen blender. In an embodiment, fluid source 120 includes a diameter index safety system ("DISS") fitting. The fluid canisters may contain gas at high pressures such as 2000 or higher and deliver gas at 280 kPa (40.6 psi) to 600 kpa (87.0 psi) by using a fluid regulator to reduce the pressure.

Fluid source connection 130, or patient airway connection 130, includes any tube or hose capable of connecting to fluid source 120 and inlet valve 180. For example, fluid source connection 130 can include a supply hose made of polyvinyl chloride ("PVC"). In another example, fluid source connection 130 can include a supply hose made of rubber.

Patient circuit connection 140 includes any tube or hose capable of connecting to output valve 170 and delivery device 150. For example, patent circuit connection 140 can include corrugated tubing. The tubing can be manufactured from a material such as ethylene-vinyl acetate ("EVA").

In an embodiment, the tubing used for patient circuit connection 160 is a continuous piece that includes sections capable of being separated from one another to form shorter pieces. For example, patient circuit connection 160 can be separated at any point approximately 6" from any other point so that any length that is an increment of 6" can be made from the continuous tube.

Figure 9:
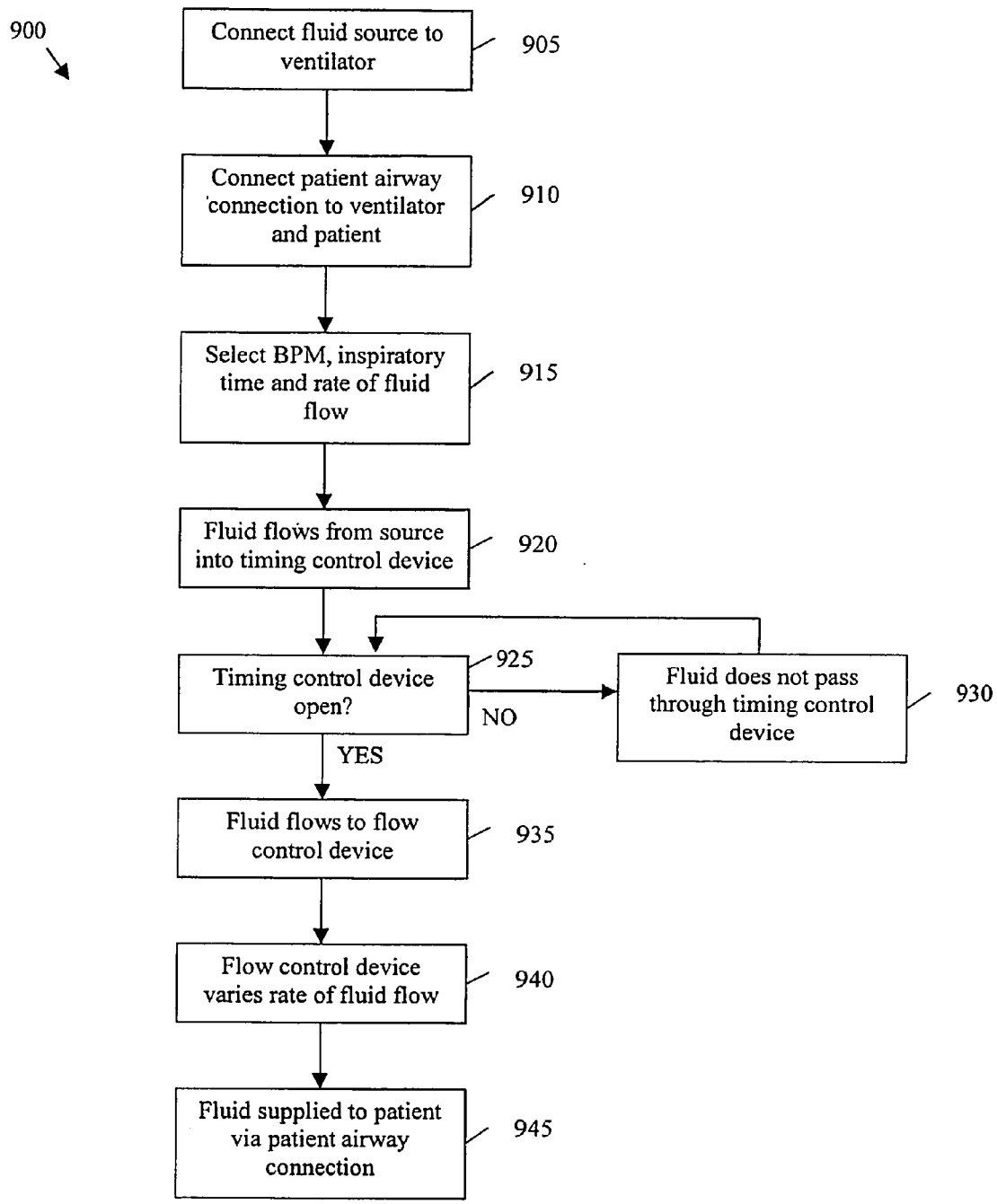
FIG. 9 illustrates a flowchart of a method for using an improved ventilator in accordance with an embodiment of the presently described invention.

FIGS. 10A and 10B illustrate two views 910, 920 of sectional tubing 930 capable of being used as patient circuit connection 160 in accordance with an embodiment of the presently described invention. As shown in FIG. 9, a plurality of tubing sections 930 (as shown in view 910) can be separated from a longer, continuous connection 160 (as shown in view 920).

Delivery device 150 includes any apparatus, device or system capable of receiving fluid from ventilator 110 via patient connection circuit 140 and delivering or providing the fluid to patient 160. For example, delivery device 150 can include an oxygen mask or endotracheal tube. In an embodiment, delivery device 150 includes an oxygen mask with a 22 mm inside diameter. In another embodiment, delivery device 150 includes an endotracheal tube with a 15 mm outside diameter.

Output valve 170 includes any outlet, valve, connection or opening capable of providing fluid communication between ventilator 110 and patient communication circuit 140. For example, output valve 170 can include a valve providing a connection between ventilator 110 and patient connection circuit 140 that permits fluid to flow from ventilator 110 to patient connection circuit 140. In an embodiment, output valve 170 includes a 22 mm connection valve. In an embodiment, output valve 170 includes an anti-suffocation valve.

Input valve 180 includes any outlet, valve, connection or opening capable of providing fluid communication between fluid source connection 130 and ventilator 110. For example, input valve 180 can include a valve providing a connection between fluid source connection 130 and ventilator 110 that permits fluid to flow from fluid source connection 130 to ventilator 110. In an embodiment, input valve 180 includes a DISS fitting. In an embodiment, input valve 180 includes a filter. For example, input valve 180 can include a 65 micron sintered bronze filter.

In operation, fluid source 120 and ventilator 110 are connected to opposing ends of fluid source connection 130. Fluid source connection 130 can be connected to input valve 180 attached to ventilator 110.

Ventilator 110 and delivery device 150 are connected to opposing ends of patient circuit connection 140. Patient circuit connection 140 can connect to output valve 170 attached to ventilator 110.

A user selects an inspiratory time ("$I_t$"). The details of how a user selects the inspiratory time are described below. In short, a user employs one or more buttons on ventilator 110 to select one of a plurality of inspiratory times. In an embodiment, a user selects a one or two second inspiratory time. For example, a user can select a one second inspiratory time for using ventilator 110 on a child or adult with a tidal volume requirement of 600 mL or less. In another example, a user can select a two second inspiratory time for using ventilator 110 on an adult with a tidal volume requirement of more than 400 mL.

A user also selects breaths per minute ("BPM"). The details of how a user selects the BPM are described below. In short, a user employs one or more buttons on ventilator 110 to select one of a plurality of BPMs. In an embodiment, a user selects a BPM from eight to thirty. In an embodiment, the range of available BPMs can be limited based on the inspiratory time selected by the user. For example, for a one second inspiratory time, the range of available BPMs can be eight to thirty or twelve to twenty. In another example, for a two second inspiratory time, the range of available BPMs can be eight to twenty or eight to twelve.

A user also selects a tidal volume ("$T_v$"). The selected tidal volume determines a rate of flow of fluid through ventilator 110 and/or delivered to patient 150. The details of how a user selects the tidal volume are described below. In short, a user employs a knob of ventilator 110 to select one of a plurality of tidal volumes. In an embodiment, the available tidal volumes and corresponding rate of flow is limited based on the selected inspiratory time. For example, the tidal volume settings available for a user to select and the corresponding rate of flow can be limited to those shown in the below table:

| Tidal Volume Setting ("$T_v$") in mL | | Rate of Flow in Liters per |
|---|---|---|
| $I_t$ = 1 second | $I_t$ = 2 seconds | Minute ("LPM") |
| 200 | 400 | 12 |
| 240 | 480 | 14.4 |
| 280 | 560 | 16.8 |
| 320 | 640 | 19.2 |
| 360 | 720 | 21.6 |
| 400 | 800 | 24 |
| 440 | 880 | 26.4 |
| 480 | 960 | 28.8 |
| 520 | 1040 | 31.2 |
| 560 | 1120 | 33.6 |
| 600 | 1200 | 36 |

The user then connects ventilator 110 to patient 160 using patient connection circuit 140 and delivery device 150. Ventilator 110 then provides tidal volumes to patient 160 at the selected BPMs. In an embodiment, if patient 160 begins to breathe spontaneously or on his or her own, the anti-suffocation valve included in output valve 170 permits ambient air to be pulled in through valve 170. In another embodiment, a sensor capable of detecting a spontaneous patient breath can be added to output valve 170. Such a sensor can detect a spontaneous breath by detecting negative pressure in output valve 170. When negative pressure is so detected, ventilator 110 then provides the selected tidal volumes to patient 160 and adjusts the timing to continue at the selected BPMs after the spontaneous breath is delivered.

In an embodiment, ventilator 110 includes a plurality of alarms. For example, ventilator 110 can include one or more alarms that become activated when a fluid or gas pressure in patient connection circuit 130 (or patient airway connection 130) exceeds a threshold (or upper airway pressure threshold), fluid or gas pressure in patient connection circuit 130 (or patient airway connection 130) falls below a threshold (or lower airway pressure threshold), the pressure of the fluid or gas supplied by source 120 falls below a threshold (or source pressure threshold), and/or a level of the power source for ventilator 110 falls below a threshold (or power source threshold). Two or more of these thresholds can be the same numeric value or can be different from the other thresholds. The details on how these alarms function is described in more detail below. Each alarm can include a visual and/or audible notification such as a light and/or a buzzer. In an embodiment, ventilator 110 can include a button or switch on control panel 210 or an alarm panel 220 that stops one or more activated alarms. For example, a button or switch similar to time control buttons 216 or BPM control buttons 218 can be pressed to dim a light or end a buzzer that is activated as an alarm. In an embodiment, pressing the button or switch to stop the alarm temporarily stops the alarm for a given time period. After the given time period, the alarm will resume if the event for which the alarm was first activated has not been remedied. In another embodiment, pressing the button or switch to stop the alarm only stops an audible alarm but does not stop any visual alarm.

In an embodiment, the threshold or upper airway pressure threshold for the fluid or gas pressure in patient connection circuit 130 is less than or equal to 52 cm $H_2O$ (5.1 kPa). That is, the upper airway pressure threshold is no more than 52 cm $H_2O$ (5.1 kPa). For example, the threshold can be 52 cm $H_2O$ (5.1 kPa).

In an embodiment, ventilator 110 can include a safety pressure relief mechanism. This mechanism can relieve pressure in ventilator 110 when the internal pressure exceeds the upper airway pressure threshold. The safety pressure relief mechanism can be embodied in a pressure relief plate, spring and outlet port. For example, the safety pressure relief mechanism can be embodied in pressure relief plate 630, spring 635 and outlet port 640 described below with respect to device 434 and FIG. 6.

In an embodiment, an alarm that occurs when the pressure in patient airway connection 130 exceeds a threshold ends or is cleared when a predetermined amount of time passes with the upper airway pressure being lower than the threshold. In other words, after the pressure in connection 130 exceeds the upper airway pressure threshold, the alarm is activated and stays active (that is, continues with an audible and/or visual notification to a user). The alarm continues in its active state until the pressure drops below the upper airway pressure threshold and stays below the threshold for a predetermined amount of time. For example, if the pressure drops below a threshold of 52 cm $H_2O$ (5.1 kPa) for at 25 seconds, the alarm ends or becomes cleared.

In an embodiment, the lower airway pressure threshold for the fluid or gas pressure in patient connection circuit 130 is 5 cm $H_2O$ (493 Pa). In addition, there can be a minimum time span at which the fluid pressure in the patient connection circuit 130 must be at or below the threshold before the alarm is activated. For example, the alarm can be set not to activate unless the pressure in patient connection circuit 130 is at or below 5 cm $H_2O$ (493 Pa) for at least 15 seconds.

In an embodiment, the alarm that is activated when the pressure of the fluid or gas supplied by source 120 falls below a threshold of 40 psi (275 kPa). In another embodiment, this threshold is 38 psi (262 kPa). In addition, the alarm can remain activated until this pressure rises above the predetermined threshold for a predetermined amount of time. In an embodiment, this amount of time is 15 seconds.

In an embodiment, the alarm that is activated when the level of the power source for ventilator 110 falls below a threshold becomes activated when a minimum amount of time of power is left in the source. That is, the alarm is triggered when the power source can only power ventilator 110 for a minimum amount of time. The minimum amount of time can be calculated by determining the voltage level remaining in the power source capable of operating ventilator 110 for the minimum amount of time. In an embodiment, this minimum amount of time is two hours. In other words, this alarm is activated when only two hours of battery power remains to power ventilator 110. In another embodiment, the alarm is triggered when the voltage remaining in the power source falls below a threshold. For example, the alarm can be triggered when a predetermined amount of voltage remains in one or more battery power sources. These power source alarms can be deactivated or cleared when the power source is replenished so that more than the predetermined minimum amount of time or voltage remains in the power source.

In an embodiment, one or more of these alarms is a visual indicator, such as a light. For example, an alarm can be a light emitting diode ("LED") that is illuminated when the alarm is activated and is not illuminated when the alarm is not activated. In another embodiment, one or more of these alarms is an audible notification. For example, an alarm can be a beep or repeated beeping sound that occurs when the alarm is activated and is silent when the alarm is not activated.

Figure 2:
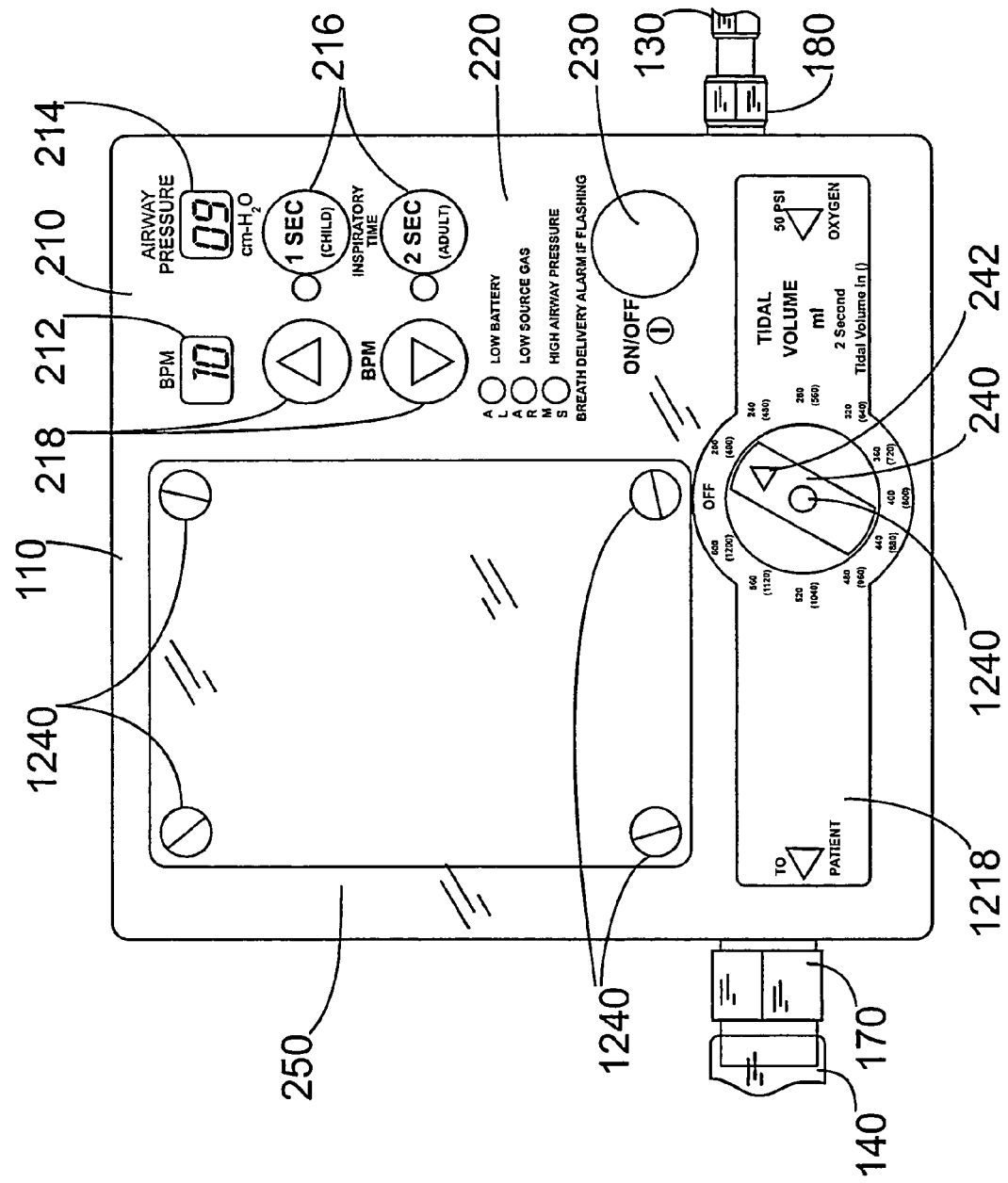
FIG. 2 illustrates a view of the ventilator in accordance with an embodiment of the presently described invention.

FIG. 2 illustrates a view of ventilator 110 in accordance with an embodiment of the presently described invention. Ventilator 110 includes a control panel 210, an alarm panel 220, an on/off switch 230, a tidal volume control knob 240 and a power source door 250.

Control panel 210 includes a BPM display window 212, an airway pressure window 214, inspiratory time control buttons 216 (also referred to as inspiratory buttons 216) and BPM control buttons 218 (also referred to as BPM buttons 218). While only two buttons are shown for each of inspiratory buttons 216 and BPM buttons 218, a larger number of buttons can be used for either set of buttons in accordance with an embodiment of the presently described invention.

Alarm panel 220 includes one or more visual indicators of one or more alarms. In the embodiment shown in FIG. 2, alarm panel 220 includes three LEDs, one for each of the high airway pressure alarm, the low source gas (or fluid pressure) alarm and the low battery (or power source) alarm. In addition, one or more of the LEDs can flash to indicate a low pressure alarm (such as when the fluid or gas pressure in patient airway connection 130 falls and stays below a threshold for a given amount of time. For example, this time can be 15 seconds, but other times can be used.

Figure 3:
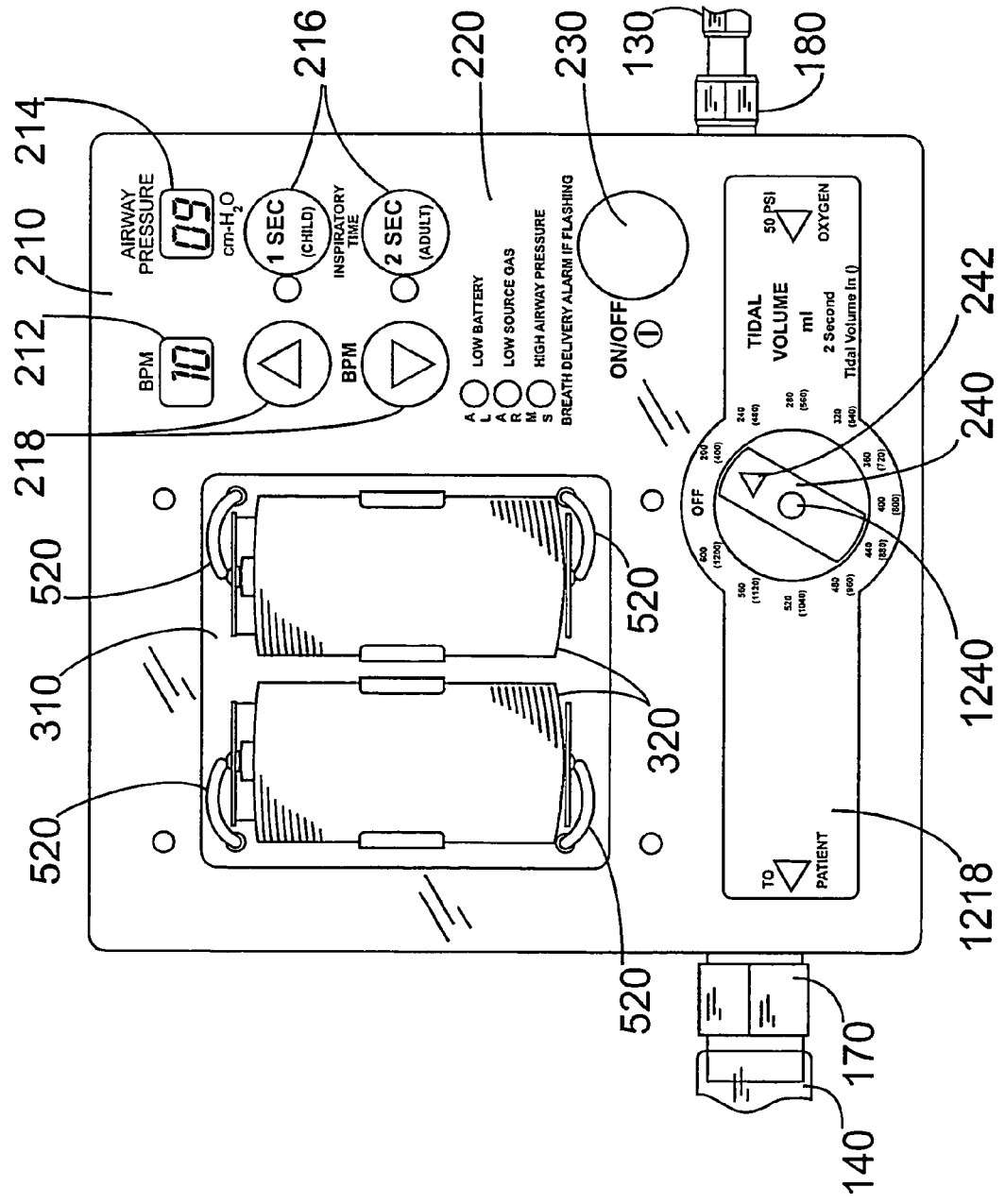
FIG. 3 illustrates a view of the power source chamber of the ventilator device in accordance with an embodiment of the presently described invention.

FIG. 3 illustrates a view of a power source chamber 310 of ventilator 110 in accordance with an embodiment of the presently described invention. Power source chamber 310 is a recessed area of ventilator 110 that is configured to hold and electrically connect an electric power source to ventilator 110. In an embodiment, chamber 310 can be accessed by removing power source door 250. For example, power source chamber 310 can include a recess with electrical connections or wires 520 for one or more power sources 320, as shown in FIG. 3.

In an embodiment, device 110 includes an electrical timing system or device (described in more detail below) that is capable of operating off of a relatively small amount of voltage or current. For example, the electrical timing device can operate off of 3.0 volts or less of direct current.

In an embodiment, power sources 320 include alkaline batteries. For example, the electrical timing device can operate off of the voltage or current supplied by two size "D" alkaline batteries. By enabling the timing device to operate off of common alkaline batteries, is becomes considerably more simple to find a power source 320 for ventilator device 110 in an emergency situation. In addition, existing ventilators use lead acid batteries as electrical power sources. These batteries are large, heavy and difficult to find when compared to alkaline batteries. While two size "D" alkaline batteries can be used, other types and combination of batteries can also be used. For example, a single alkaline or lithium battery (or any other battery capable of providing voltage), or any combination of batteries capable of providing the minimum voltage required to operate ventilator 110 can be used. In an embodiment, ventilator 110 can be supplied with three or less volts by one or more batteries. These volts can be stepped up by a voltage step-up circuit. Alternatively, ventilator 110 can be supplied with more than three volts by one or more batteries and not require any voltage step-up circuitry.

In an embodiment, power source(s) 320 enables the timing device of ventilator 110 to operate for at least eight hours at room temperature, assuming that a fluid source 120 does not expire before the eight hours is completed. In a preferred embodiment, power source(s) 320 enable the timing device to operate continuously for at least eight hours at room temperature (again, assuming fluid source 120 does not become depleted before then). In a more preferred embodiment, two alkaline batteries (such as size "D" alkaline batteries, for example) acting as power sources 320 enable the timing device to operate continuously for at least eight hours at room temperature (again, assuming fluid source 120 does not become depleted before then).

In an embodiment, power source(s) 320 enables the timing device of ventilator 110 to operate for at least twelve hours at room temperature, assuming that a fluid source 120 does not expire before the twelve hours is completed. In a preferred embodiment, power source(s) 320 enable the timing device to operate continuously for at least twelve hours at room temperature (again, assuming fluid source 120 does not become depleted before then). In a more preferred embodiment, two alkaline batteries (such as size "D" alkaline batteries, for example) acting as power sources 320 enable the timing device to operate continuously for at least twelve hours at room temperature (again, assuming fluid source 120 does not become depleted before then).

In an even more preferred embodiment, power source(s) 320 enable the timing device to operate for at least forty-eight hours at room temperature (again, assuming fluid source 120 does not become depleted before then). In an even more preferred embodiment, power source(s) 320 enable the timing device to operate continuously for at least forty-eight hours at room temperature (again, assuming fluid source 120 does not become depleted before then). In an even more preferred embodiment, two alkaline batteries (such as size "D" alkaline batteries, for example) acting as power sources 320 enable the timing device to operate continuously for at least forty-eight hours at room temperature (again, assuming fluid source 120 does not become depleted before then). By "operating" and "operate," it is meant that power source 320 provides sufficient power to ventilator 110 so that ventilator 110 can deliver one or more breaths to a patient 160.

In an embodiment, on/off switch 230 is used to activate or deactivate circuit 514. That is, when switch 230 is pressed so as to turn ventilator 110 "on," power is supplied to circuit 514 from power source 320. Conversely, when switch 230 is pressed so as to turn ventilator 110 "off," power is no longer supplied to circuit 514 from power source 320.

Figure 12:
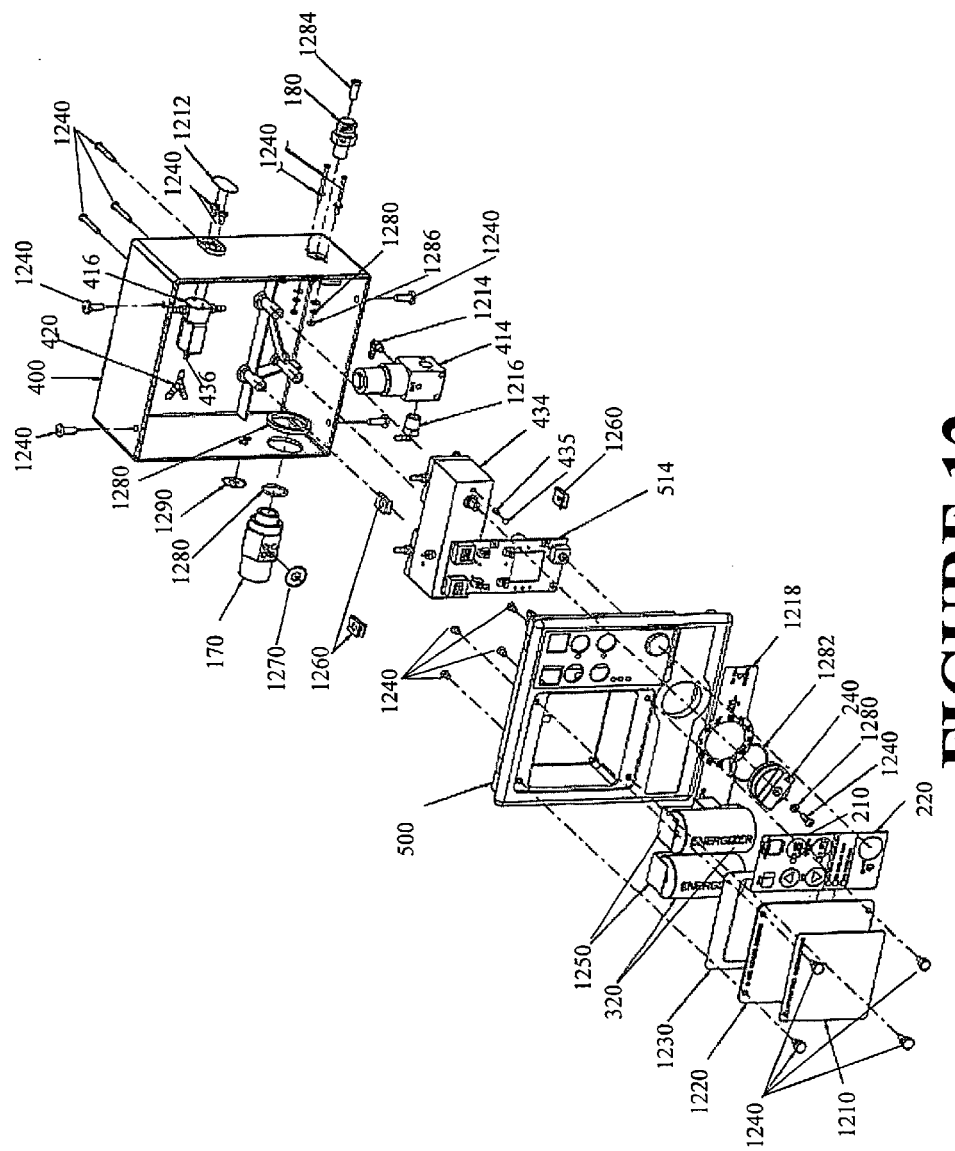
FIG. 12 illustrates an exploded view of the ventilator in accordance with an embodiment of the presently described invention.

FIG. 12 illustrates an exploded view of ventilator 110 in accordance with an embodiment of the presently described invention. Ventilator 110 includes a plurality of panels 1210, 1220 and 1230, a plurality of screws 1240, power source 320, a plurality of electrical contacts 1250, two halves 400 and 500 of ventilator 11 housing, a plurality of clips 1260, output valve 170, an antisuffocation valve 1270, a plurality of washers 1280, a pressure relief valve 1290, a screw cover 1212, an elbow fitting 1214, a ball and spring combination 435, a regulator connector 1216, circuit 514, flow control device 434, regulator 414, input/inlet valve 180, solenoid 416, Y-connector 420, solenoid barb 436, a decal 1218, knob 240, control panel 210, alarm panel 220 and an o-ring 1282. Ventilator 110 also can include one or more filters 1284 and/or nuts 1286. Filters 1284 can be inserted into an input or output orifice of ventilator 10. For example, a filter 1284 can be inserted into input valve 180 to filter out some or all impurities in the fluid supplied to ventilator 110 through input valve 180.

Panels 1210, 1220 and 1230 can be combined to form power source door 250.

Subsets of plurality of screws 1240 are configured to perform several functions. For example, screws 1240 can be used to: (a) hold panels 1210, 1120 and 1230 together and to enclose power source chamber 310, (b) hold ventilator halves 400, 500 together using clips 1260, (c) hold solenoid 416 in place in one half of ventilator housing 400, (d) connect knob 240 with protrusion 610 and/or (e) mount flow control device 434 to housing 400. As shown in FIG. 12, different sizes and lengths of screws 1240 can be used to achieve the various functions listed above, as well as other functions. Additionally, one or more screws 1240 can be used in combination with one or more nuts 1286 in order to provide a more secure connection, as shown in FIG. 12.

Electrical contacts 1250 are each configured (or configured to operate together) to permit power to be transferred from power source 320 to wires 520. For example, electrical contacts 1250 can be sections of an electrically-conductive material (such as a metal) connected to poles of batteries as power source 320 and to wires 520.

Various ones of the plurality of washers 1280 are configured and placed to provide an improved seal around the components each is placed around or against, as shown in FIG. 12, and/or to hold one or more screws 1240 in place. Also as shown in FIG. 12, washers 1280 can be different sizes in order to accommodate different sized components, openings or screws 1240 in ventilator 110.

O-ring 1282 is placed to create a partial or complete seal around knob 240. By placing o-ring 1280 as shown in FIG. 12, o-ring 1282 can impede and/or prevent water or other fluids from entering ventilator 110 near knob 240.

Screw cover 1212 is configured to be placed over screws 1240 that hold solenoid 416 in place. Cover 1212 can cover these screws 1240 for protection of screws 1240 from static discharge and/or tampering, and for a more aesthetically pleasing appearance.

Regulator connector 1216 is configured to provide a fluid communication path from regulator 414 to tube 426. Fitting 1214 is another connector that is similar to connector 1216. Fitting 1214 comprises an elbow with a barb on one end and a thread on the other end. Fitting 1214 can be identical to connector 1216 with a different thread size. The barb includes an outlet such as a tube or other opening in fitting 1214.

Decal 1218 is configured to provide visual reference marks so a user can know which direction to rotate knob 240 and how far to rotate knob 240 to obtain a desired flow rate through device 434. In other words, decal 1218 can include markings of flow rates that correspond to an orifice 622 selected by rotating knob 240 to a given position, as shown in FIGS. 1 and 2.

Antisuffocation valve 1270 is a valve capable of opening to allow outside atmosphere (for example, air) to patient 160 via connection circuit 140. Valve 1270 can be configured so as to only provide outside atmosphere to patient 166 if patient 160 attempts to breath on his or her own and ventilator 110 is off or otherwise unable to deliver a breath to patient 160 at that time.

Valve 1290 is a valve capable of impeding or preventing a buildup of pressure inside ventilator 110. For example, the fluid provided to patient 160 by ventilator 110 can leak into the inside of ventilator 110. When this occurs, the fluid pressure inside ventilator 110 can buildup. In order to prevent this buildup of pressure from damaging ventilator 110 or any components of ventilator 110, valve 1290 can open when the fluid pressure exceeds a predetermined threshold and permit the fluid inside ventilator 110 to escape to the surrounding atmosphere.

Ball and spring combination 435 includes a ball connected to one end of a spring. Combination 435 is inserted in flow control device 434 so that the ball of combination 435 sticks out of device 434. Knob 240 can include a plurality of indentations on the back side of knob 240. These indentations are preferably located to match up with each of a plurality of markings 242 on knob 240 (described in more detail below). By rotating knob 240, ball and spring combination 435 push a ball against the indentations in knob 240. As the indentations pass by combination 435, a user who is rotating knob 240 can feel and/or hear the ball as it is pressed in each of the indentations. In addition, the ball and spring combination 435 can hold knob 240 in place when it is rotated into a desired position.

The function and location of the remaining components in FIG. 12 are described below and/or shown in the attached Figures.

Figure 4:
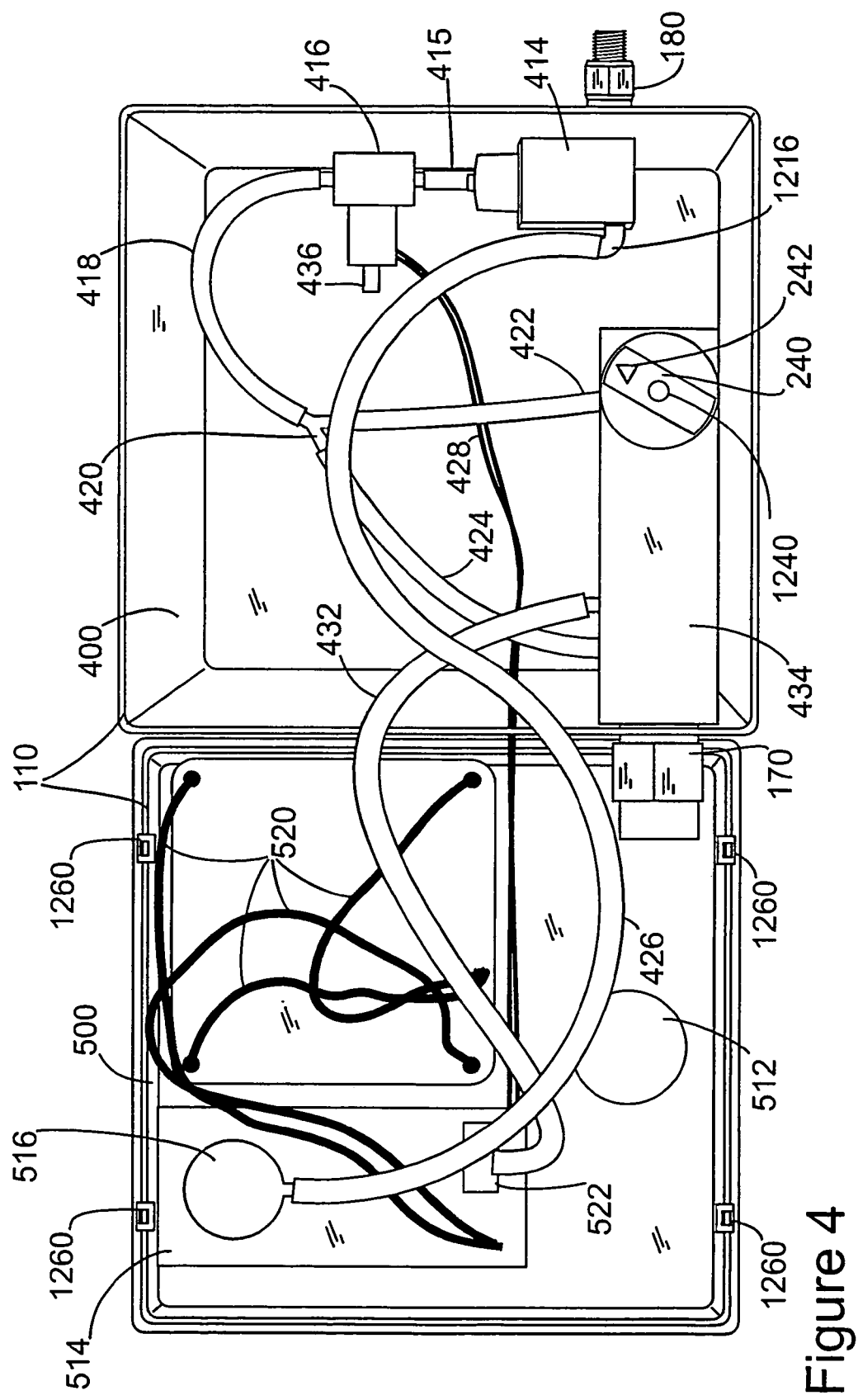
FIG. 4 illustrates a view of inside the ventilator in accordance with an embodiment of the presently described invention.
Figure 4A:
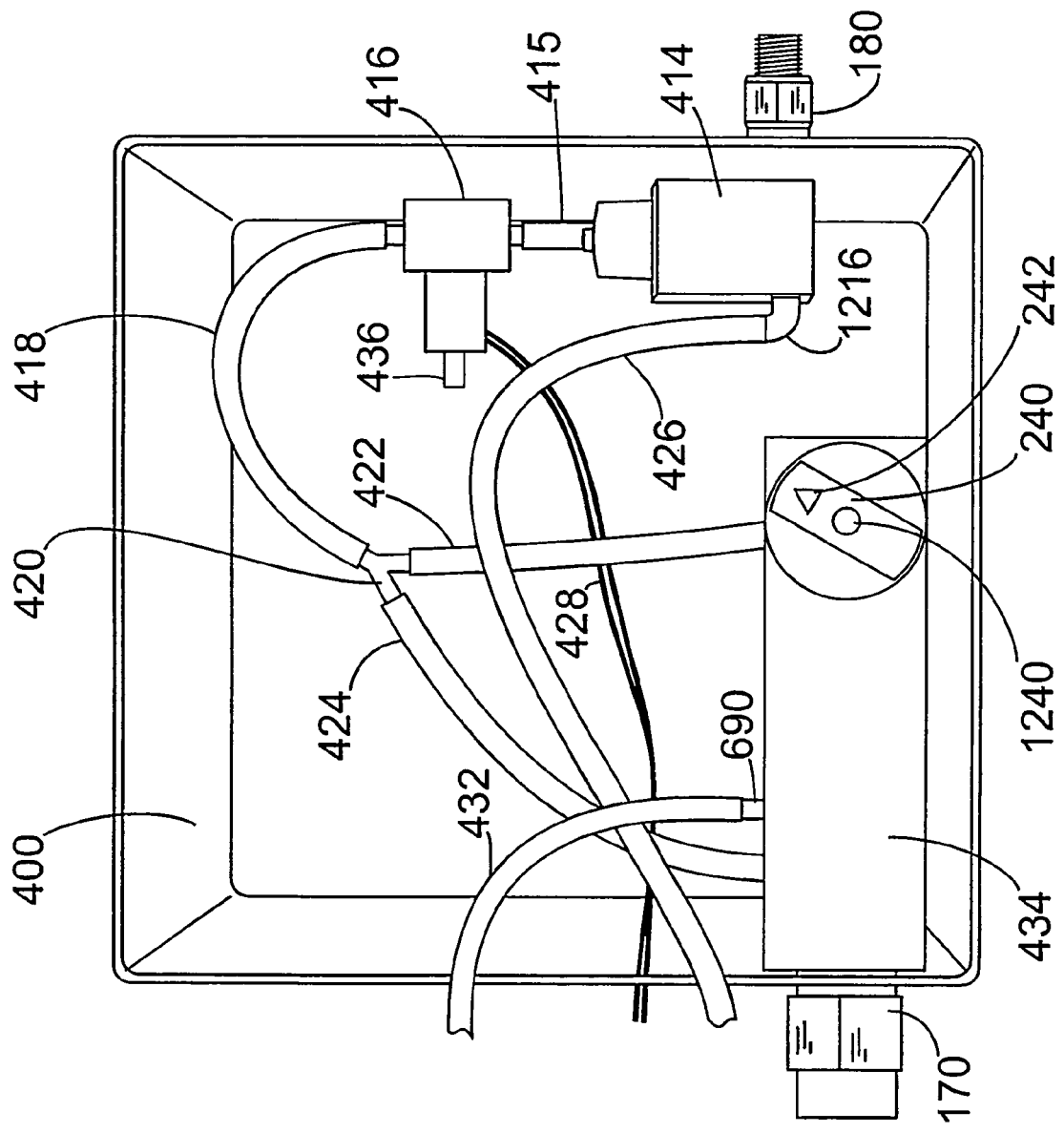
FIG. 4A illustrates a view of one half of the inside of the ventilator in accordance with an embodiment of the presently described invention.
Figure 4B:
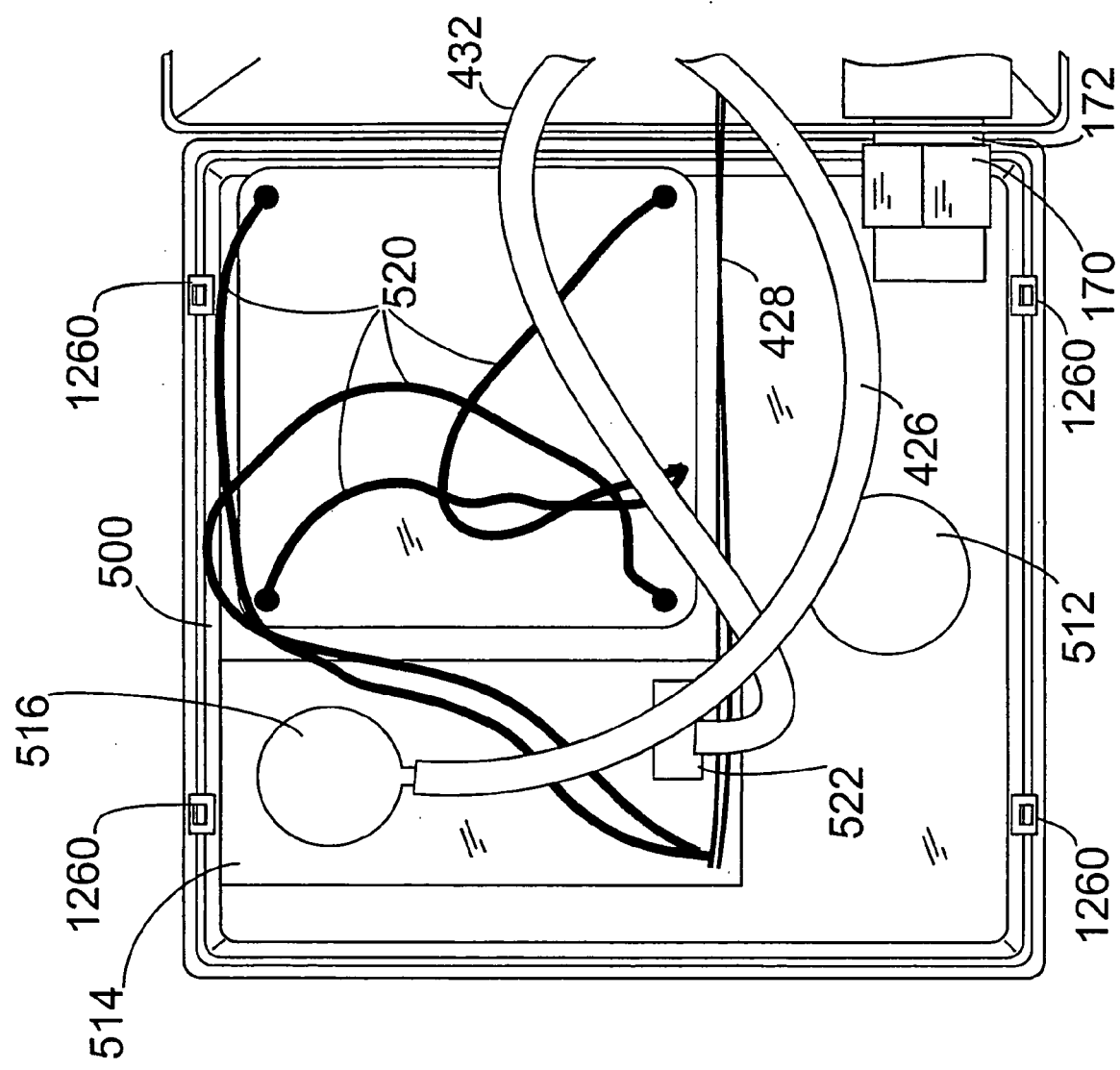
FIG. 4B illustrates a view of the other half of the inside of the ventilator in accordance with an embodiment of the presently described invention.

FIG. 4 illustrates a view of inside ventilator 110 in accordance with an embodiment of the presently described invention. FIG. 4A illustrates a view of one half of ventilator 110 housing 400 and of the insides of ventilator device 110 in accordance with an embodiment of the presently described invention. FIG. 4B illustrates a view of the other half of ventilator 110 housing 500 and of the insides of ventilator device 110 in accordance with an embodiment of the presently described invention.

Insides 400, 500 of ventilator device 110 include a pressure regulator 414, a solenoid 416, a plurality of tubes (referred to as first tube 418, second tube 422, third tube 424, fourth tube 426, fifth tube 518, sixth tube 432 and seventh tube 415), a tube connector 420, one or more solenoid 416 control wires 428, a flow control device 434, one or more power source 320 wires 520, one or more electrical circuits 514, holes 172, 512, a plurality of sensors (referred to as first sensor 516 and second sensor 522), and a plurality of clips 1260. Circuit(s) 514 is/are referred to as circuit 514, regardless of whether circuit 514 comprises one or more electrical circuits.

First sensor 516 can include a pressure switch configured to close when the measured pressure falls within a particular range. For example, first sensor 516 can include a pressure switch that closes when the measured pressure is between 38 and 40 psi (262 and 275 kPa). First sensor 516 can be monitored for the low source pressure alarm described above. In an embodiment, first sensor 516 can include a printed circuit board mount pressure and vacuum switch, such as the switch manufactured by Presairtrol and designated by part number CSPEGA-10PR(60 4).

Second sensor 522 can include a pressure sensor capable of measuring a range of pressures and providing a voltage signal as output. For example, sensor 522 can measure a range of pressures from 0 to 60 cm $H_2O$ (0 to 5.9 kPa). In an embodiment, second sensor 522 can include an integrated silicon pressure sensor, such as the sensor manufactured by Freescale Semiconductor, Inc. with the series number MPXV4006G.

As described above, a fluid source 120 is connected to ventilator 110 via fluid source connection 130 and inlet valve connection 180. Regulator 414 is connected to inlet valve 180. Regulator 414 is also connected to solenoid 416 and fourth tube 426. Regulator 414 is connected to sensor 516 via tube 426.

Solenoid 416 is connected to regulator 414 using tube 415, one or more wires 428 and first tube 418. Solenoid 416 is electrically connected to circuit 514 via wire(s) 428. Solenoid 416 is connected to flow control device 434 via first tube 418, connector 420, second tube 422 and third tube 424.

Connector 420 connects first tube 418 with second and third tubes 422, 424. In an embodiment, connector 420 is a Y-connector.

Flow control device 434 is connected to tidal volume control knob 240, second tube 422, third tube 424, sixth tube 432 and output valve 170. Flow control device 434 is connected to solenoid 416 via tubes 418, 422 and 424 and connector 420. Flow control device 434 is connected to circuit 514 and sensor 516 via tube 432. Flow control device 434 is also connected to patient 160 via output valve 170, patient circuit connection 140 and delivery device 150.

FIGS. 5A, 5B, 5C, and 5D illustrate several views 530, 540, 550 and 560 of flow control device 434 in accordance with an embodiment of the presently described invention. View 530 is a perspective view of a back side and top of flow control device 434. View 540 is a perspective view of a front side and top of device 434. View 550 is a plan view of a side of device 434. View 560 is a plan view of the back side of device 434.

Figure 6:
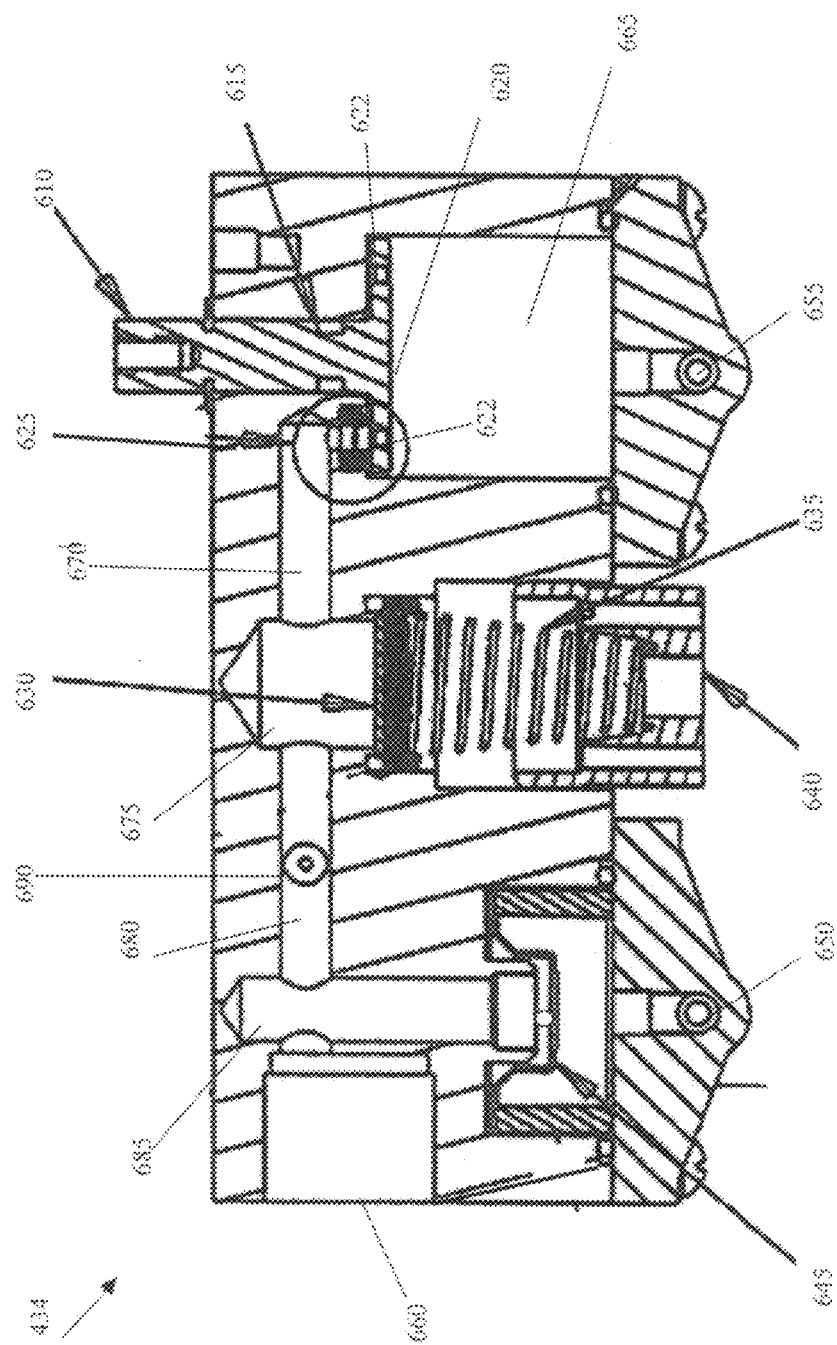
FIG. 6 illustrates a cross-sectional view of the flow control device in accordance with an embodiment of the presently described invention.

FIG. 6 illustrates a cross-sectional view of flow control device 434 in accordance with an embodiment of the presently described invention. Flow control device 434 includes a knob connector 610, an orifice control tube 615, an orifice plate 620, an orifice connection 625, a pressure relief plate 630, a spring 635, a pressure relief outlet port 640, a diaphragm valve 645, an exhalation port 650, an input port 655 and an output port 660. An interior of device 434 also includes a plurality of chambers and tubes through which pressurized fluid can pass through. These chambers and tubes include an entry chamber 665, a first tube 670, a middle chamber 675, a second tube 680 and a third tube 685.

In an embodiment, orifice connection 625 is sealed by one or more O-rings surrounding connection 625. These o-rings can prevent or impede fluid from passing around, rather than through, connection 625.

Knob connector 610 includes any object or protrusion capable of interfacing with knob 240. For example, connector 610 can include an object that fits inside of knob 240 so that rotating knob 240 also causes connector 610 to rotate.

Knob connector 610 is connected to tube 615. Tube 615 is also connected to orifice plate 620. In this way, tube 615 connects knob connector 610 to orifice plate 620. By turning knob 240 when it is connected to connector 610, connector 610, tube 615 and orifice plate 620 also rotate. In an embodiment, a plurality of connector 610, tube 615 and orifice plate 620 are integrally formed of the same material. That is, a plurality of these components is part of a single object and cannot be separated from one another without damaging or destroying the object.

Input port 655 is in fluid communication with first chamber 665. By "fluid communication" or "fluidly connected," it is meant that a fluid can pass from the components, chambers and/or tubes that are so connected. Therefore, a fluid such as pressurized $O_2$ can pass from input port 655 to first chamber 665. In an embodiment, input port 655 is capable of being connected to tube 422. In this way, fluid traveling through tube 422 can enter into first chamber 665.

First chamber 665 is in fluid communication with first tube 670 via orifice connection 625. Orifice connection 625 includes an orifice selected by rotating orifice plate 620 to a given position. As described in more detail below, orifice plate 620 includes a plurality of orifices 622 having a plurality of different diameters.

First tube 670 is in fluid communication with middle chamber 675. In an embodiment, device 434 includes a pressure relief apparatus. The pressure relief apparatus includes pressure relief plate 630, spring 635 and pressure relief outlet port 640. The pressure relief apparatus acts to relieve a build up of pressure in device 434. The pressure of the fluid traveling through device 434 can build up and push plate 630 against spring 635. If the fluid pressure becomes large enough to overcome the force of spring 635 pushing plate 630 against the fluid pressure, plate 630 moves towards outlet port 640. When outlet port 640 is moved far enough so that the fluid in middle chamber 675 can travel out of outlet port 640, the pressure in device 434 can decrease. The fluid pressure in middle chamber 675 continues to decrease until the force of spring 635 pushing plate 630 against the fluid pressure overcomes the fluid pressure. At that point, plate 630 closes the path of the fluid from middle chamber 675 to outlet port 640 and the fluid travels from middle chamber 675 to second tube 680.

The fluid travels from second tube 680 to third tube 685 and outlet port 660. Outlet port 660 is configured to connect to valve 170. The fluid can travel into outlet port 660, through valve 170 and into patient connection circuit 140.

Figure 11:
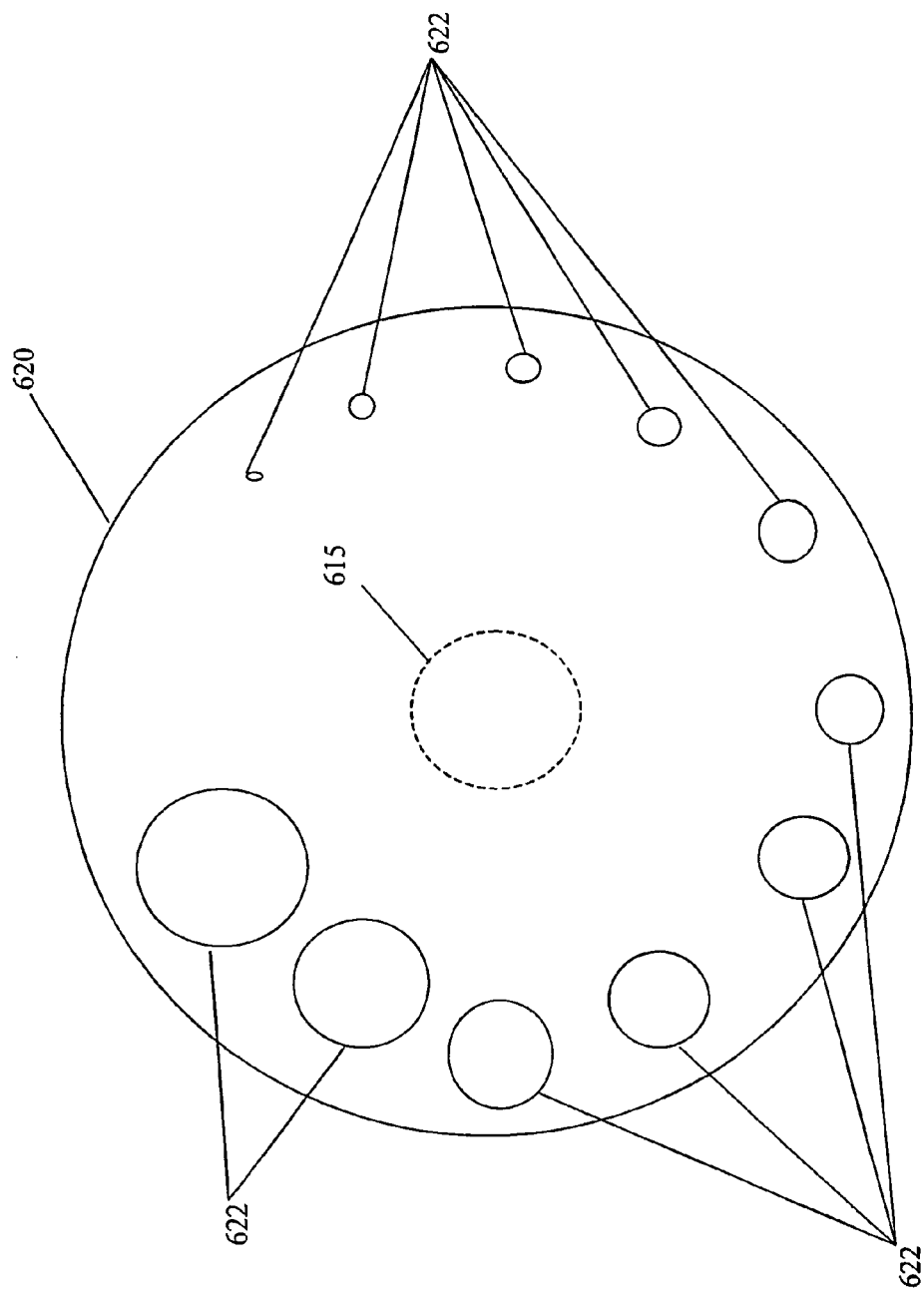
FIG. 11 illustrates an orifice plate in accordance with an embodiment of the presently described invention.

FIG. 11 illustrates orifice plate. 620 in accordance with an embodiment of the presently described invention. As shown in FIG. 11, orifice plate 620 includes a plurality of orifices 622 each having a different diameter. As the diameter of each orifice 622 can affect the rate of fluid flow through orifice plate 620, by changing which orifice 622 the fluid passes through device 434, the rate of flow of the fluid delivered to patient 160 can be varied. That is, by rotating plate 620 to each of a plurality of positions, each of the plurality of orifices can be placed in a position to provide a connection (or orifice connection 625) between chamber 665 and tube 670. As the diameter of the orifice used in connection 625 changes by a user rotating knob 240, the rate of flow of the fluid passing through device 434 and ventilator 110 can be varied. In an embodiment, orifice plate 620 can include one or more locations on plate 620 where no orifices 622 exist. That is, instead of having an orifice 622 in a location where one would normally be located, plate 620 can be solid in that location. When this location is lined up with orifice connection 625, flow of the fluid through device 434 can be impeded or blocked.

In an embodiment of the presently described invention, device 434 includes an outlet port 690 useful for measuring a pressure of the fluid passing through device 434. As shown in FIGS. 10A and 10B, outlet port 690 is in fluid communication with tube 680. Fluid traveling through tube 680 can also pass through outlet port 690. As described below, fluid traveling through outlet port 690 passes into tube 432, which is configured to direct sufficient fluid in device 434 and/or patient connection circuit (or patient airway connection) 140 to sensor 522 so that sensor 522 can measure the fluid pressure in connection circuit 140 and/or device 434.

As shown in FIGS. 4, 4A, 4B, 5A, 5B, 5C, and 5D, ports 650, 655 and 690 can be connected to tubes 424, 422 and 432, respectively. That is, tube 424 can be placed onto port 650 to establish fluid communication between port 650 and at least connector 420. Tube 422 can likewise be placed onto port 655 to establish fluid communication between port 655 and at least connector 420. Tube 432 can also be placed onto port 690 to establish fluid communication between port 690 and sensor 522. By making these connections, fluid travel travels throughout ventilator 110. For example, fluid can exit solenoid 416 and travel through tube 422. As tube 422 connects to port 655, the fluid can enter device 434 via port 655.

In an embodiment, pressure relief outlet port 640 does not connect to any tube or connector. Outlet port 640 can instead direct fluid traveling through it into interior of ventilator 110 or outside of ventilator 110 via one or more holes or other outlet(s) lined up with port 640.

Knob 240 and hole 512 are configured so that when the two halves 400, 500 of ventilator 110 are combined together, or closed together, to form ventilator 110 as shown in FIG. 1. Knob 240 can be accessible through hole 512.

Valve 170 and hole 172 are configured so that when the two halves 400, 500 of ventilator 110 are combined together, or closed together, to form ventilator 110 as shown in FIG. 1. Valve 170 can be accessible through hole 172.

Wires 520 connect one or more power sources 320 to circuit 514. Sensors 516, 522 are each connected to or a part of circuit 514. In an embodiment, circuit 514 is a printed circuit board ("PCB") housing one or more electrical circuits. Using a PCB for circuit 514 makes the electrical components of ventilator 110 more durable than existing ventilators that include non-PCB based electrical components. In addition, the PCB can be sprayed or otherwise coated with an epoxy to add further strength and durability to circuit 514 and therefore ventilator 110.

In an embodiment, circuit 514 is capable of comparing one or more measured quantities to one or more thresholds to determine if any of the alarms described above need to be activated. For example, circuit 514 is connected to power source 320 by wires 520. From this connection, circuit 514 can obtain electrical power and measure the voltage, current or time remaining in power source 320. In an embodiment, circuit 514 can calculate the amount of time remaining by comparing a remaining amount of voltage in power source 320 and comparing this voltage to previous testing results. The previous testing results can include tests on how long ventilator 110 was able to run on a given amount of remaining voltage. For example, during testing a given voltage remaining in power source 320 can yield two hours of operation by ventilator 110. Circuit 514 can calculate the amount of time remaining by comparing the existing amount of voltage in power source 320 and comparing it to the minimum voltage required for two hours of operation.

In another example, one or more of sensors 516, 522 can determine or measure a fluid pressure and communicate the pressure to circuit 514. Circuit 514 can then compare the pressure to one or more thresholds (described above) and activate one or more alarms:

In an embodiment, circuit 514 includes a voltage step up circuit. The voltage step up circuit can increase the supplied voltage to circuit 514 from power source 320. For example, circuit 514 can include a voltage step up circuit that increases a voltage of 3.0 volts supplied by two size "D" alkaline batteries to 5.0 volts. The 5.0 volts can then be applied to selected electrical components.

In addition, in an embodiment circuit 514 is in communication with BPM buttons 218 and inspiratory buttons 216. For example, electrical contacts or connections between circuit 514 and buttons 216, 218 can provide such communication. Circuit 514 can include programmable logic functionality that is capable of being simply programmed by a user. For example, circuit 514 can include one or more processors or microprocessors.

Circuit 514 can be capable of being controlled by a user pushing buttons 216 and/or 218. As described in more detail below, a user can increase and/or decrease the BPM administered to a patient 160 using buttons 218. When either of buttons 218 are depressed, circuit 514 changes the BPM, or frequency, of the fluid supplied to patient 160. In an embodiment, circuit 514 is also capable of illuminating or displaying the selected BPM in display window 212.

A user can also control the inspiratory time administered by ventilator 110 to patient 160 using inspiratory buttons 216. By selecting one or the other of buttons 216, a user can select whether a longer inspiratory time is required for an adult or adult-sized patient 160 or a shorter inspiratory time is required for a child or child-sized patient 160, for example. When a user selects one of buttons 216, circuit 514 changes the inspiratory time of the fluid administered to patient 160 by ventilator 110. In addition, ventilator 110 can display the selected inspiratory time. For example, circuit 514 can cause a light or LED next to one or more of buttons 216 to become illuminated when that button 216 is selected.

In operation, a fluid source 120 is connected to ventilator 110 as described above. Fluid source 120 is opened or otherwise enabled to supply fluid, such as a pressurized gas, to ventilator 110 via inlet valve 180. Once the fluid enters ventilator 110, the fluid is directed to regulator 414. Regulator 414 regulates the input fluid pressure for ventilator 110. In an embodiment, regulator 414 decreases the pressure of the input fluid. For example, regulator 414 can step down the input fluid pressure to 40 psi (275 kPa). In addition, regulator 414 can serve to provide a more uniform pressure to orifice plate 622. By providing a more uniform pressure on orifice plate 622, the rate of fluid flow through ventilator 110 can be more consistent if the pressure of the fluid supplied by source 120 varies.

A portion of the fluid passes from regulator 414 to sensor 516. In an embodiment, sensor 516 measures or otherwise determines the pressure of the fluid input to ventilator 110. Sensor 516 can measure this pressure to determine if pressure of the fluid supplied by source 120 falls below the source pressure threshold described above. In an embodiment, sensor 516 is powered by power source 320. If the pressure does fall below this threshold, sensor 516 can communicate this event with circuit 514, which can then activate an alarm. For example, the light next to the "low source gas alarm" on alarm panel 220 can be illuminated if the pressure of the source fluid drops below 40 psi (275 kPa).

A portion of the fluid also passes from regulator 414 to solenoid 416. Solenoid 416 acts as a valve that is capable of stopping or allowing the flow of the fluid to pass through ventilator 110. For example, solenoid 416 includes a piston capable of moving between as least two positions. In an embodiment, one position of the piston permits the fluid to pass through solenoid 416 and on through tube 418 while another position of the piston impedes this fluid flow or stops the flow completely.

Figure 7:
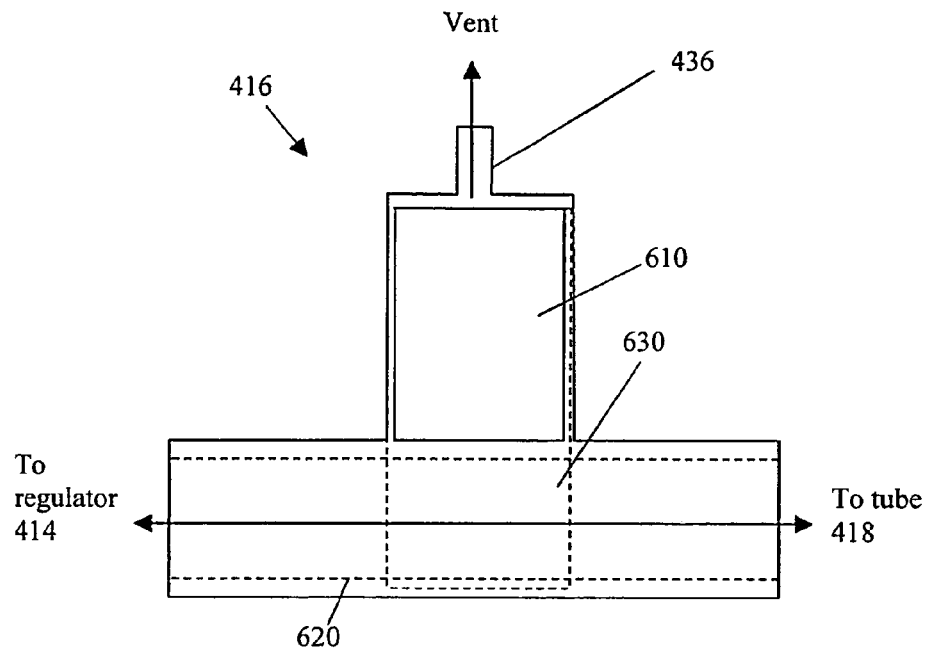
FIG. 7 illustrates a schematic diagram of a solenoid in an open position in accordance with an embodiment of the presently described invention.
Figure 8:
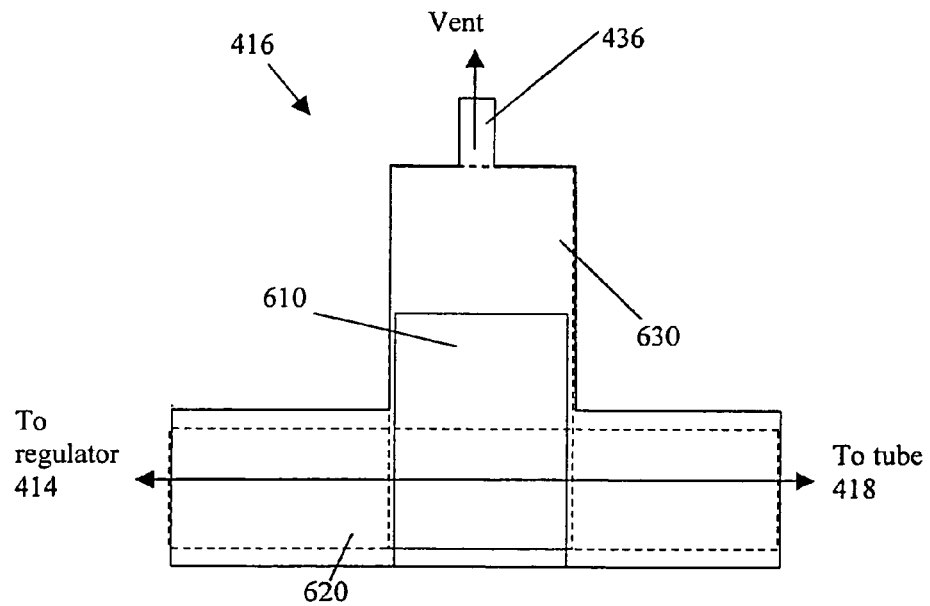
FIG. 8 illustrates a schematic diagram of a solenoid in a closed position in accordance with an embodiment of the presently described invention.

FIGS. 7 and 8 illustrate schematic diagrams of solenoid 416 in accordance with an embodiment of the presently described invention. FIGS. 7 and 8 illustrate simplified views of one embodiment of the operation of solenoid 416. Other manners of operation of solenoid 416 that achieve the same start/stop functionality (with respect to the flow of the fluid through ventilator 110) are also within the scope of embodiments of the presently described invention.

Solenoid 416 includes a piston 610, a fluid flow path 620 and a piston travel path 630. In an embodiment, piston 610 is capable of moving between a first position (shown in FIG. 7 and referred to as an "open" position) and a second position (shown in FIG. 8 and referred to as a "closed" position). Piston 610 can be moved between first and second positions using a voltage difference supplied by power source 320 and/or circuitry 514. In an embodiment, a 1.5 volt differential moves piston 610 between first and second, or open and closed, positions. The voltage differential, and therefore control of solenoid 416, can be provided via wire 418 connected to circuitry 514.

While piston 610 is in the open position, fluid is delivered to a patient 160 from ventilator 110. The fluid passes through solenoid 416 via the fluid flow path 620 with piston 610 being generally out of flow path 620.

When piston 610 is in the closed position, fluid is not being delivered to patient 160 or the fluid flow is greatly impeded. That is, fluid flow path 620 is partially to completely blocked by piston 610. In other words, while the closed position may not completely block the flow of all fluid from source 120 to patient 160, the closed position causes solenoid 416 to prevent a majority of fluid flow from reaching patient 160. In an embodiment, all fluid flow through path 620 is blocked by solenoid 416 when it is in the closed position. In such an embodiment, solenoid 416 includes a barb 436, as shown in FIGS. 4 and 4A. Barb 436 is an outlet such as a tube or other opening in solenoid 416. Barb 436 provides an outlet port that can vent the pressure in connection 140 and permit delivery device 150 to open and permit patient 160 to exhale.

In an embodiment, piston 610 is capable of only being in the open or closed position. That is, piston 610 is incapable of being halfway between the open and closed positions. In such an embodiment, solenoid 416 is only capable of permitting or blocking/impeding fluid flow through ventilator 110. In other words, solenoid 416 cannot be at a position other than the open or closed position.

Once fluid passes through solenoid 416 (assuming solenoid 416 is in an open position), the fluid travels through tube 418 to connector 420. Once fluid reaches connector 420, the fluid passes through connector 420 into tubes 422 and 424. From tubes 422, 424, the fluid travels into flow control device 434. In doing so, the path of the fluid travels first through solenoid 416 and then through flow control device 434. In other words, solenoid 416 is "upstream" from flow control device 434 and flow control device 434 is "downstream" from solenoid 416.

Figure 13:
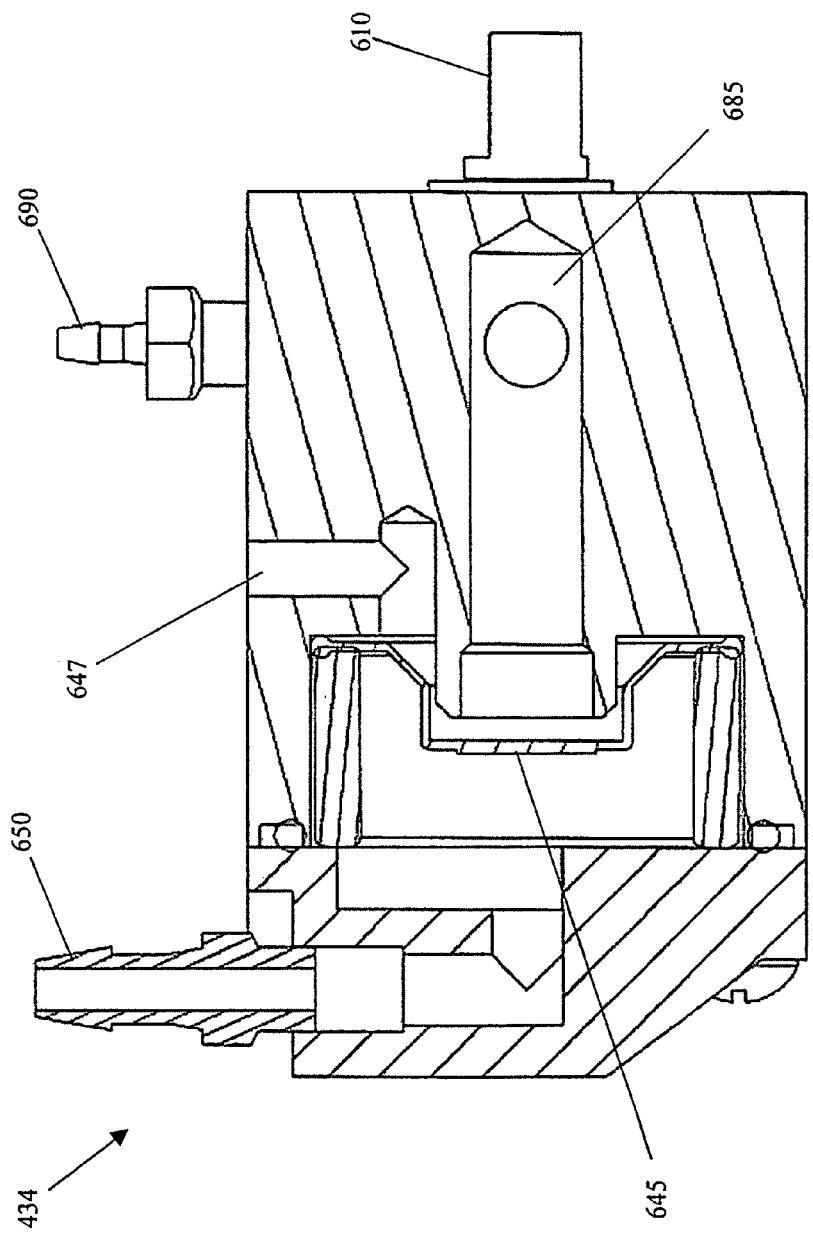
FIG. 13 illustrates a cross-section view of the flow control device in accordance with an embodiment of the presently described invention.

Solenoid 416 and flow control device 434 can operate together to make it easier for patient 160 to exhale. FIG. 13 illustrates a cross-section view of flow control device 434 in accordance with an embodiment of the presently described invention. Device 434 as illustrated in FIG. 13 is similar to the embodiment illustrated in FIGS. 5A, 5B, 5C, 5D, and 6. One difference is that device 434 in FIG. 13 includes a hole 647 connecting a chamber surrounding diaphragm valve 645 with the atmosphere surrounding flow control device 434. Hole 647 can assist in opening and/or closing diaphragm valve 645. In combination, hole 647 and diaphragm valve 645 can work together to vent patient connection circuit 140 and thus make it easier for patient 160 to exhale.

In operation, when solenoid 416 is in the open position, fluid flows from solenoid 416 into ports 650 and 655. As fluid flows into port 650, the fluid pushes diaphragm valve 645 to close. When diaphragm valve 645 is closed, fluid cannot pass or is impeded from passing from port 650 to tube 685 and hole 647. Instead, fluid passes from tube 685 into outlet port 660 and then into patient connection circuit 140. As fluid passes into connection circuit 140, one-way valve 157 remains open so that the fluid can be provided to patient 160 via patient connection circuit 140 and delivery device 150.

When solenoid 416 is in the closed position, fluid flows out of barb 436 of solenoid 416 and does not pass into port 650. When fluid does not flow into port 650, the fluid pressure forcing diaphragm valve 645 closed decreases or no longer exists. If the fluid pressure forcing diaphragm valve 645 drops to a sufficiently low level, diaphragm valve 645 opens. Once diaphragm valve 645 opens, hole 647 can provide a path of fluid communication between the atmosphere surrounding flow control device 434 and tube 685 (and therefore output port 660 and patient connection circuit 140, as each of tube 685, port 660 and circuit 140 are connected). The fluid pressure in patient connection circuit 140 is then vented through outlet port 660, tube 685 and hole 647 into the atmosphere surrounding flow control device 434. Once the fluid pressure in patient connection circuit 140 decreases a sufficient amount, one-way valve 157 closes. When valve 157 closes, patient 160 can exhale through exhalation port 155.

In an embodiment, tube 432 is in communication with patient connection circuit 140 via flow control device 434. Tube 432 is also connected to sensor 522. Tube 432 is configured to direct sufficient fluid in patient connection circuit (or patient airway connection) 140 and/or in device 434 to sensor 522 so that sensor 522 can measure the corresponding fluid pressure. Once sensor 522 measures or otherwise determines the fluid pressure, circuit 514 can compare this pressure to a threshold, such as the upper airway pressure threshold and/or the lower airway pressure threshold described above. If the fluid pressure in connection circuit or airway connection 140 exceeds the upper airway pressure threshold, for example, circuit 514 activates one or more alarms, as described above. If the fluid pressure in airway connection 140 is lower than the lower airway pressure threshold, for example, circuit 514 activates one or more alarms, also as described above. In an embodiment, an alarm includes illuminating the light next to the text "HIGH AIRWAY PRESSURE ALARM" on alarm control panel 220.

In addition, circuit 514 can cause the fluid pressure in airway connection 140 to be displayed to a user in window 214 of ventilator 110.

In an embodiment, a timing control device of ventilator includes solenoid 416, at least a functional portion of circuit 514 and power source 320. By "functional portion," it is meant that the part(s) or portion(s) of circuit 514 that controls whether solenoid 416 is in an open or closed position is the functional portion of the timing control device.

The timing control device controls the frequency (or BPM) and duration (or inspiratory time) of breaths administered by ventilator 110 using an electrical power source 320 and solenoid 416. In this manner, the timing control for ventilator 110 is electronically controlled. The functional portion of circuit 514 related to the timing control device determines, based on user input, the selected BPM and/or inspiratory time to be used in supplying the fluid to patient 160. As described above, this user input can be a user pushing BPM buttons 218 and/or inspiratory buttons 216.

Based on the BPM and/or inspiratory time selected by the user, circuit 514 determines the rate, or frequency, at which solenoid 416 should switch between open and closed positions. As described above, when solenoid 416 is in an open position, fluid is being delivered to patient 160. Conversely, when solenoid 416 is in a closed position, fluid is not being delivered to patient 160. Circuit 514 can control whether solenoid 416 is in an open or closed position by varying a voltage differential across solenoid 416. For example, by varying the voltage supplied to solenoid 416 using wire(s) 428 by 1.5 volts, circuit 514 can cause solenoid 416 to change between open and closed positions.

For example, if a BPM of ten is selected by a user (indicating ten breaths per minute), then circuit 514 can determine that solenoid 416 should open and close once every six seconds to cause ventilator 110 to deliver ten breaths in a minute. If a BPM of thirty is selected, circuit 514 can determine that solenoid 416 should open and close once every two seconds to cause ventilator 110 to deliver thirty breaths in a minute, for example. If a BPM of five is selected, circuit 514 can determine that solenoid 416 should open and close once every twelve seconds to cause ventilator 110 to deliver five breaths in a minute, for example.

In another set of examples, if an inspiratory time of one second is selected by a user (indicating that the inspiratory time, or fluid delivery time, should last for one second), then circuit 514 can determine that solenoid 416 should open and remain open for one second before closing at each breath delivered by ventilator 110. If an inspiratory time of two seconds is selected, circuit 514 can determine that solenoid 416 should open and remain open for two seconds before closing at each breath delivered by ventilator 110, for example.

Thus, circuit 514 can electrically control solenoid 416 to vary the frequency and duration of breaths supplied to patient 160 by ventilator. For example, with a BPM of ten and an inspiratory time of two seconds selected, circuit 514 can cause solenoid 416 to open and close ten times per minute and remain in an open position each time it opens for two seconds. By providing electronic control of the timing of breaths provided by ventilator 110, the timing control device of ventilator 110 provides a more accurate and precise manner of controlling the BPM and inspiratory time. As the timing control device does not rely on source 120 fluid pressure to operate (as some existing ventilators do), but instead rely on relatively long-lasting power source(s) 230, the timing control device has a greater accuracy and precision as long as an adequate power source 230 remains. That is, as the pressure of a source 120 fluid can vary to a greater extent than the voltage supplied by alkaline battery power sources 230, for example, ventilators that rely on source fluid pressure can experience greater fluctuations in their breath timing control (such as BPM and inspiratory time) than ventilator 110.

Another component of ventilator 110 is flow control device 434. Flow control device 434 enables a user to control and vary the rate at which the fluid is supplied to a patient 160 during the inspiratory time (or time at which solenoid 416 is in an open position). As described above, flow control device 434 controls the rate at which the fluid is delivered to a patient 160 using a plurality of orifices of different diameters. A user selects which orifice is to be used by turning knob 240 to a desired tidal volume (as shown in FIGS. 1 and 2). Markings on an outside surface of ventilator 110 can indicate which orifice is selected. A marking 242 on knob 240 can be employed by a user to select the desired orifice and tidal volume. In general, selecting a larger tidal volume causes a greater rate of fluid flow through flow control device 434 and to patient 160.

As described above, flow control device 434 does not rely on any electricity, electric power source or electrical circuits. Thus, device 434 does not rely on, and is not controlled or otherwise dependent upon power source 230 and circuit 514. As a result, device 434 is essentially a pneumatic flow control of ventilator 110, and is generally more robust and durable than electrically controlled flow controls in existing ventilators.

Using flow control device and the timing control device, a user can very accurately and precisely control the volume of fluid delivered to a patient by ventilator 110. That is, the user can control the BPM and inspiratory time that a selected rate of fluid is provided to a patient 160. As a result, the separate timing control device and flow control devices of ventilator 110 permit a user to electronically control a time period at which a selected rate of fluid flow is provided to patient 160.

As described above, ventilator 110 includes a timing control device that operates off a low voltage power circuit. This timing control device can be powered by relatively longer lasting, light, small, inexpensive and readily available alkaline batteries, for example. This improves over existing ventilators that rely on relatively heavy, large and expensive lead acid batteries that have a relatively shorter life and are relatively difficult to find (especially in emergency situations). This design of ventilator 110 can reduce its overall weight compared to existing ventilators and can increase the operating time of ventilator 110 over existing ventilators.

Moreover, by separating the timing control device and flow control device 434 into separately controlled devices operated electrically and pneumatically, respectively, ventilator 110 can provide increased accuracy and precision in BPM and inspiratory times for fluids provided to patients 160. Existing ventilators may include all pneumatic systems to control fluid flow and timing. Such ventilators typically include complex pneumatic systems that rely on the build up of source fluid pressure as a timing function (or as a timing control device). But, small leaks and slight variations common in these ventilators can affect the performance, accuracy and precision of the ventilators.

In addition, some existing ventilators are entirely electronically controlled. Such ventilators use electronic circuits to control the timing and to control and drive a complex proportioning valve to establish flow control of fluid through the ventilator. Such ventilators typically require more power or voltage than embodiments of ventilator 110. In addition, these ventilators typically require additional hardware such as position feedback circuits to obtain improved accuracy in their timing.

FIG. 9 illustrates a flowchart of a method 900 for using an improved ventilator 110 in accordance with an embodiment of the presently described invention. Method 900 begins at step 905, where a fluid source is connected to the ventilator. For example, a source 120 can be connected to ventilator 110 as described above.

Next, at step 910 a patient airway connection is connected to the ventilator and to a patient. For example, patient airway connection 140 can be connected to ventilator 110 and patient 160 as described above.

Next, at step 915, a BPM, inspiratory time and rate of fluid flow are selected. For example, a user can select a desired BPM and inspiratory time using buttons 216, 218 and can select a rate of fluid flow by turning knob 240 to a desired tidal volume, as described above.

Next, at step 920, the fluid flows from the fluid source into a timing control device of the ventilator. For example, the fluid can flow from source 120 into solenoid 416, as described above. In an embodiment, the fluid can flow into a pressure regulator, such as regulator 414, prior to flowing into the timing control device.

Next, at step 925, method 900 proceeds to either step 930 or step 935 depending on whether the timing control device is open or in an opened state. If the timing control device is open, then method 900 proceeds from step 925 to step 935. If the timing control device is closed, then method 900 proceeds from step 925 to step 930. For example, if solenoid 416 is in an open state or position, method 900 can proceed from step 925 to step 935. If solenoid 416 is in a closed state or position, method 900 can proceed from step 925 to step 930.

At step 930, the fluid does not pass through the timing control device. That is, the timing control device blocks or at least impedes a majority of the fluid flow through the timing control device. For example, solenoid 416 can block or impede the flow of the fluid through solenoid 416. Method 900 proceeds from step 930 back to step 925, where it is determined whether the timing control device is open. In doing so, method 900 proceeds in a loop including steps 925 and 930 until the timing control device is in an open position or state.

At step 935, the fluid passes through the timing control device and into the flow control device. For example, as described above, the fluid can pass into flow control device 434 after passing through an open solenoid 416.

Next, at step 940, the flow control device varies the rate of fluid flow. That is, the flow control device can increase or decrease the rate of fluid flow. In an example, flow control device 434 includes a plurality of orifices having different diameters. Flow control device 434 can direct the flow of fluid through one or more of these orifices to change the rate of fluid flow, as described above.

Next, at step 945, the fluid is supplied to a patent. For example, the fluid can be supplied to a patient 160 after passing through flow control device 434 via a patient airway connection 140.

While particular elements, embodiments and applications of the presently described invention have been shown and described, it is understood that the presently described invention is not limited thereto since modifications may be made by those skilled in the technology, particularly in light of the foregoing teaching. It is therefore contemplated by the appended claims to cover such modifications and incorporate those features that come within the spirit and scope of the presently described invention.

The invention claimed is:

1. A ventilator including:
   a manually adjustable and electrically powered timing control device capable of controlling a period of time that a fluid is delivered to a patient during each of several inspiratory time periods, said timing control device including a solenoid and an outlet, said timing control device configured to be manually adjusted by an operator to change said inspiratory time periods that said fluid is delivered to said patient, wherein said timing device moves said solenoid to a position to block flow of said fluid to said patient during time between a plurality of said inspiratory time periods with said outlet directing said fluid flowing through said timing control device away from said patient during said time between said plurality of said inspiratory time periods; and
   a flow control device controlling a rate of flow that said fluid is delivered to said patient, said flow control device including a plurality of orifices configured to be adjusted to change said rate of said flow that said fluid is delivered to said patient during each of said inspiratory time periods.

2. The ventilator of claim 1, wherein said timing control device is disposed upstream of said flow control device along a pathway that said fluid flows to said patient.

3. The ventilator of claim 1, wherein said timing control device is electrically powered to start or stop said flow of said fluid to said patient by a plurality of replaceable alkaline batteries.

4. The ventilator of claim 1, wherein said timing control device controls durations of said inspiratory time periods by actuating said solenoid to an open position or a closed position, each of said inspiratory time periods beginning when said solenoid is actuated to said open position and ending when said solenoid is actuated to said closed position, said solenoid configured to permit flow of said fluid to said patient when said solenoid is at said open position and impede said flow of said fluid when in said closed position.

5. The ventilator of claim 1, wherein said flow control device controls said rate of flow by permitting said fluid to pass through at least one of said plurality of orifices, said orifices including a plurality of different diameters.

6. The ventilator of claim 1, wherein a volume of fluid provided to said patient by said timing control device and said flow control device is capable of being altered by manually adjusting one or more of said inspiratory time periods using said timing control device or by manually adjusting said rate of flow using said flow control device.

7. The ventilator of claim 1, wherein said flow control device includes an inlet that is fluidly coupled with said timing control device to receive said fluid from said timing control device, a first outlet fluidly configured to be fluidly coupled with said patient to deliver said fluid to said patient, and a different second outlet, further comprising a patient airway pressure sensor configured to be fluidly coupled with said second outlet of said flow control device, said pressure sensor configured to measure a pressure of said fluid delivered to said patient through said first outlet of said flow control device based on at least some of said fluid that flows to said pressure sensor through said second outlet of said flow control device.

8. The ventilator of claim 7, further including at least one alarm communicatively coupled with said pressure sensor and configured to provide at least one of a visual notification or an audible notification when at least one of a plurality of events occurs, said events including one or more of:
   (a) said pressure of said fluid exceeding an upper airway pressure threshold;
   (b) said pressure of said fluid falling below a lower airway pressure threshold for at least a predetermined period of time; or
   (c) said pressure at which said fluid is supplied by said fluid source falling below a source pressure threshold.

9. The ventilator of claim 7, wherein said second outlet of said flow control device does not direct said fluid to said patient.

10. The ventilator of claim 1, further comprising a plurality of manual inputs communicatively coupled with said timing control device, said manual inputs including an inspiratory time control device and a breaths per minute device, said timing control device configured to be actuated by said operator to change a duration of one or more of said inspiratory time periods, said breaths per minute device configured to be actuated by said operator to change a frequency of said inspiratory time periods.

11. A ventilator including:
   an inspiratory timing control device configured to be fluidly coupled with a patient airway connection that delivers a fluid to a patient, said timing control device configured to start and stop a flow of said fluid to said patient through said patient airway connection, said timing control device powered by at least one battery and configured to receive manual input from an operator that directs said timing control device when to start or stop said flow of said fluid to said patient;

a flow control device fluidly coupled with said timing control device and with said patient airway connection, said flow control device having a first outlet configured to be fluidly coupled with said patient airway connection, a plurality of orifices having different diameters, and a different second outlet, said flow control device configured to receive said fluid from said timing control device and control a rate of said flow of said fluid to said patient through said first outlet and said patient airway connection; and a patient airway pressure sensor fluidly coupled with said second outlet of said flow control device, said patient airway sensor configured to receive at least some of said fluid passing through one or more of said orifices of said flow control device and exiting said flow control device through said second outlet, said pressure sensor measuring a pressure of said fluid delivered to said patient based on said fluid received from said second outlet.

12. The ventilator of claim 11, wherein said timing control device is configured to calculate a time period required to deliver a desired tidal volume of said fluid to said patient at a manually selected rate of fluid flow based on said manual input, said timing control device further configured to control a start and end to said time period by moving a solenoid between first and second positions.

13. The ventilator of claim 11, wherein said timing control device is powered by one or more replaceable batteries.

14. The ventilator of claim 11, wherein said timing control device is configured to start and stop said flow of said fluid to said flow control device at a point upstream from said plurality of orifices in said flow control device.

15. The ventilator of claim 11, further comprising a plurality of manual inputs communicatively coupled with said timing control device, said manual inputs including an inspiratory time control device and a breaths per minute device, said inspiratory time control device configured to be actuated by said operator to change said period of time of one or more of said inspiratory time periods, said breaths per minute device configured to be actuated by said operator to change a frequency of said inspiratory time periods.

16. The ventilator of claim 11, wherein said timing control device includes a solenoid and an outlet, said timing control device configured to move said solenoid to a position to block flow of said fluid to said patient with said fluid flowing through said timing control device directed away from said patient and out of said timing control device through said outlet of said timing control device when said solenoid blocks said flow of said fluid.

17. The ventilator of claim 11, wherein said second outlet of said flow control device does not direct said fluid to said patient.

18. A method of providing a ventilator, the method comprising:

providing an inspiratory timing control device configured to be fluidly coupled with a patient airway connection that delivers a fluid to a patient, said control device configured to start and stop a flow of said fluid to said patient through said patient airway connection;

fluidly coupling a flow control device with said timing control device and with said patient airway connection, said flow control device having a first outlet configured to be coupled with said patient airway connection, a plurality of orifices having different diameters, and a second outlet, said flow control device configured to receive said fluid from said timing control device and control a rate of said flow of said fluid to said patient through said first outlet and said patient airway connection; and fluidly coupling a patient airway pressure sensor with said second outlet of said flow control device, said patient airway sensor configured to receive at least some of said fluid passing through one or more of said orifices of said flow control device and exiting said flow control device through said second outlet, said pressure sensor measuring a pressure of said fluid delivered to said patient based on said fluid received from said second outlet.

19. The method of claim 18, wherein providing said timing control device includes providing an outlet in said timing control device such that at least some of said fluid is directed out of said timing control device and away from said patient through said outlet in said timing control device when said timing control device stops said flow of said fluid to said patient through said patient airway connection.

20. The method of claim 18, wherein fluidly coupling said flow control device includes fluidly coupling said flow control device such that a desired tidal volume is delivered to said patient at a selected rate of fluid flow through said flow control device, said flow control device configured to calculate a time period required to deliver said desired tidal volume at said selected rate of fluid flow based on said manual input and controlling a start and end to said time period by moving a solenoid between first and second positions.

21. The method of claim 18, wherein further comprising powering said flow control device with one or more replaceable batteries.

22. The method of claim 18, wherein fluidly coupling said flow control device includes fluidly coupling said flow control device downstream of said timing control device such that said timing control device is configured to start and stop said flow of said fluid at a point upstream from said plurality of orifices in said flow of said fluid through said flow control device.

* * * * *